(12) United States Patent
Manfredi

(10) Patent No.: US 6,562,576 B2
(45) Date of Patent: May 13, 2003

(54) YEAST TWO-HYBRID SYSTEM AND USE THEREOF

(75) Inventor: John Manfredi, Salt Lake City, UT (US)

(73) Assignee: Myriad Genetics, Inc., Salt Lake City, UT (US)

( * ) Notice: Subject to any disclaimer, the term of this patent is extended or adjusted under 35 U.S.C. 154(b) by 0 days.

(21) Appl. No.: 10/040,910

(22) Filed: Jan. 4, 2002

(65) Prior Publication Data

US 2002/0106698 A1 Aug. 8, 2002

Related U.S. Application Data

(60) Provisional application No. 60/259,759, filed on Jan. 4, 2001.

(51) Int. Cl.[7] .................... G01N 33/567; G01N 33/569; C07H 21/04; C12N 1/14; C12N 15/00
(52) U.S. Cl. ................................ 435/6; 435/4; 435/7.1; 435/7.31; 435/69.1; 435/69.7; 435/69.9; 435/471; 435/476; 435/481; 435/483; 435/320.1; 435/243; 435/252.3; 435/254.1; 435/255.1; 536/23.1; 536/23.4
(58) Field of Search .................... 435/7.1, 7.2, 7.31, 435/7.4, 4, 6, 29, 34, 69.1, 69.9, 71.1, 471, 476, 479, 480, 481, 483, 243, 252.3, 254.1, 255.1, 320.1; 536/22.1, 23.1, 23.4, 24.1

(56) References Cited

U.S. PATENT DOCUMENTS

| | | | | |
|---|---|---|---|---|
| 5,283,173 A | * | 2/1994 | Fields et al. .................... 435/6 |
| 5,637,463 A | * | 6/1997 | Dalton et al. ............. 435/320.1 |
| 5,695,941 A | * | 12/1997 | Brent et al. ............. 435/254.21 |
| 5,834,247 A | | 11/1998 | Comb et al. |
| 5,885,779 A | * | 3/1999 | Sadowski et al. ......... 435/254.2 |
| 5,981,182 A | | 11/1999 | Jacobs, Jr. et al. |
| 6,057,091 A | | 5/2000 | Beachy et al. |
| 6,294,330 B1 | * | 9/2001 | Michnick et al. ......... 435/252.3 |
| 6,365,347 B1 | * | 4/2002 | Murray et al. ............ 435/320.1 |

OTHER PUBLICATIONS

Ozawa, et al. A Fluorescent Indicator for Detecting Protein-Protein Interactions in Vivo Based on Protein Splicing. Anal. Chem. 72, p. 5151–5157 (2000).*
Remy, I. and Michnick, S. W. Clonal selection and in vivo quantitation of protein interactions with protein–fragment complementation assays. Proc. Natl. Acad. Sci., U.S.A. 96, p. 5394–5399 (1999).*
U.S. patent application Ser. No. 10/040,967, Manfredi, filed Jan. 4, 2002.
U.S. patent application Ser. No. 10/040,969, Manfredi, filed Jan. 4, 2002.
U.S. patent application Ser. No. 10/040,964, Manfredi et al., filed Jan. 4, 2002.
Chong, Shaorong, et al., "Protein Splicing Involving the Saccharomyces cerevisiae VMA Intein", The Journal of Biological Chemistry, Sep. 6, 1996; 271(36):22159–22168.
Wu, Hong, et al., "Protein trans–splicing and functional mini–inteins of a cyanobacterial dnaB intein", Biochimica et Biophysica Acta,1998; 1387:422–432.
Shingledecker, Kaori, et al., "Molecular dissection of the Mycobacterium tuberculosis RecA intein: design of a minimal intein and of a trans–splicing system involving two intein fragments", Gene, 1998; 207:187–195.
Severinov, Konstantin, et al., "Expressed Protein Ligation, a Novel Method for Studying Protein–Protein Interactions in Transcription", The Journal of Biological Chemistry, Jun. 26, 1998; 273(26):16205–16209.
Wu, Hong, et al., "Protein trans–splicing by a split intein encoded in a split DnaE gene of Synechocystis sp. PCC6803", Proc. Natl. Acad. Sci. USA, Aug. 1998; 95:9226–9231.
Lew, Belinda M., et al., "Characteristics of Protein Splicing in trans Mediated by a Semisynthetic Split Intein", Biopolymers, 1999; 51:355–362.
Xu, Rong, et al., "Chemical ligation of folded recombinant proteins: Segmental isotopic labeling of domains for NMR studies", Proc. Natl. Acad. Sci. USA, Jan. 1999; 96:388–393.
Evans, Thomas C., Jr., et al., "The in Vitro Ligation of Bacterially Expressed Proteins Using an Intein from Methanobacterium thermoautotrophicum", The Journal of Biological Chemistry, Feb. 12, 1999; 274(7):3923–3926.
Amitai, Gil, et al., "Fine–tuning an engineered intein", Nature Biotechnology, Sep. 1999; 17:854–855.
Evans, Thomas C., Jr., et al., "Protein trans–Splicing and Cyclization by a Naturally Split Intein from the dnaE Gene of Synechocystis Species PCC6803", The Journal of Biological Chemistry, Mar. 31, 2000; 275(13):9091–9094.
Ozawa, Takeaki, et al., "A Fluorescent Indicator for Detecting Protein–Protein Interactions in Vivo Based on Protein Splicing", Analytical Chemistry, Nov. 1, 2000; 72(21):5151–5157.
Ozawa, Takeaki, et al., "Split Luciferase as an Optical Probe for Detecting Protein–Protein Interactions in Mammalian Cells Based on Protein Splicing", Analytical Chemistry, Jun. 1, 2001; 73(11):2516–2521.
Karimova, Gouzel, et al., "A Bacterial Two–Hybrid Based on a Reconstituted Signal Transduction Pathway", Proc. Natl. Acad. Sci., May 1998; 95:5752–5756.

* cited by examiner

Primary Examiner—David Guzo
Assistant Examiner—David A. Lambertson
(74) Attorney, Agent, or Firm—Jay Z. Zhang; Myriad IP Dept.

(57) ABSTRACT

A method for detecting protein-protein interactions is provided, in which two fusion proteins are prepared and allowed to interact with each other in yeast cells. The interaction between the two fusion proteins leads to protein trans-splicing, generating an active and detectable reporter.

28 Claims, 15 Drawing Sheets

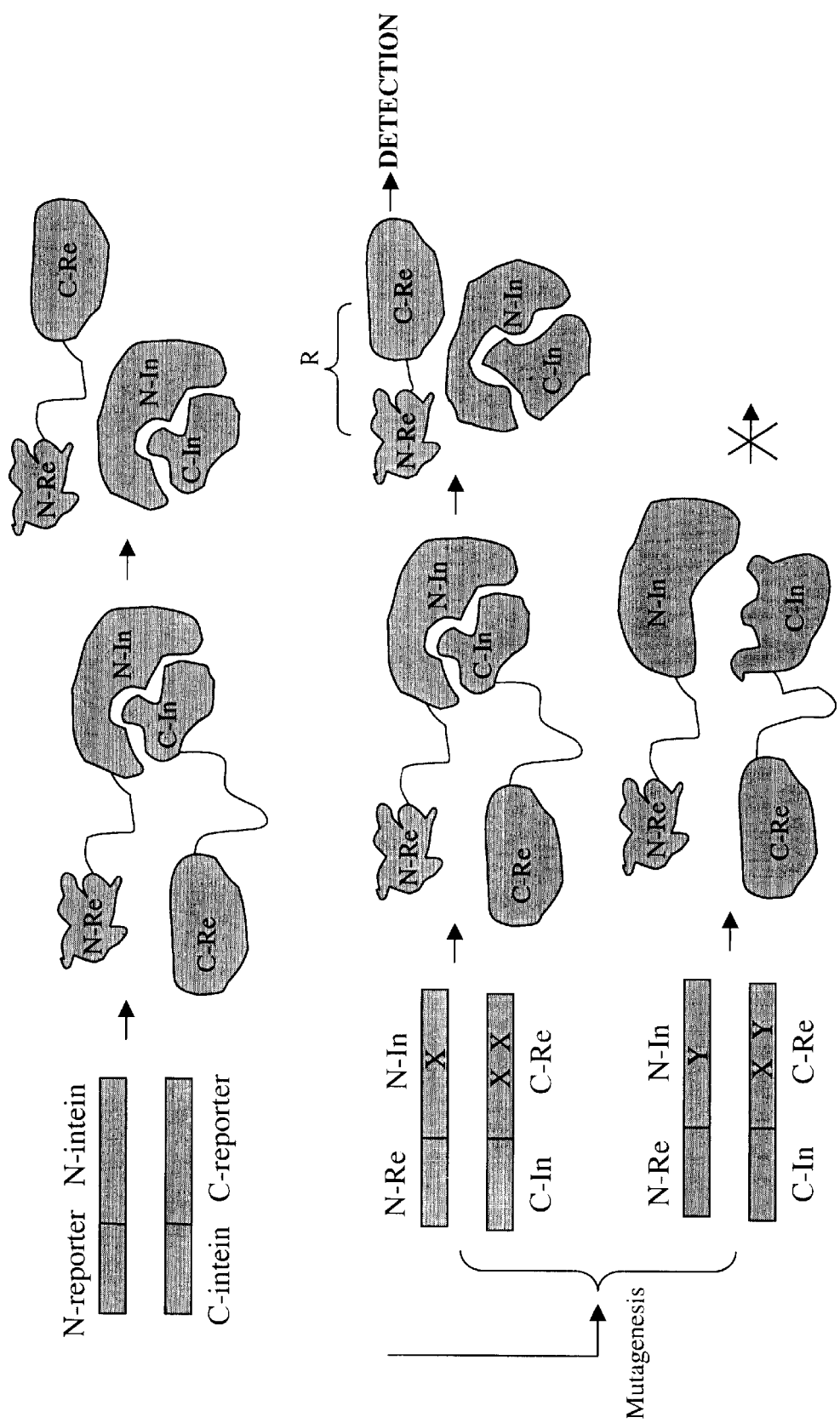
Figure 2A Selecting Non-interacting N-intein & C-intein

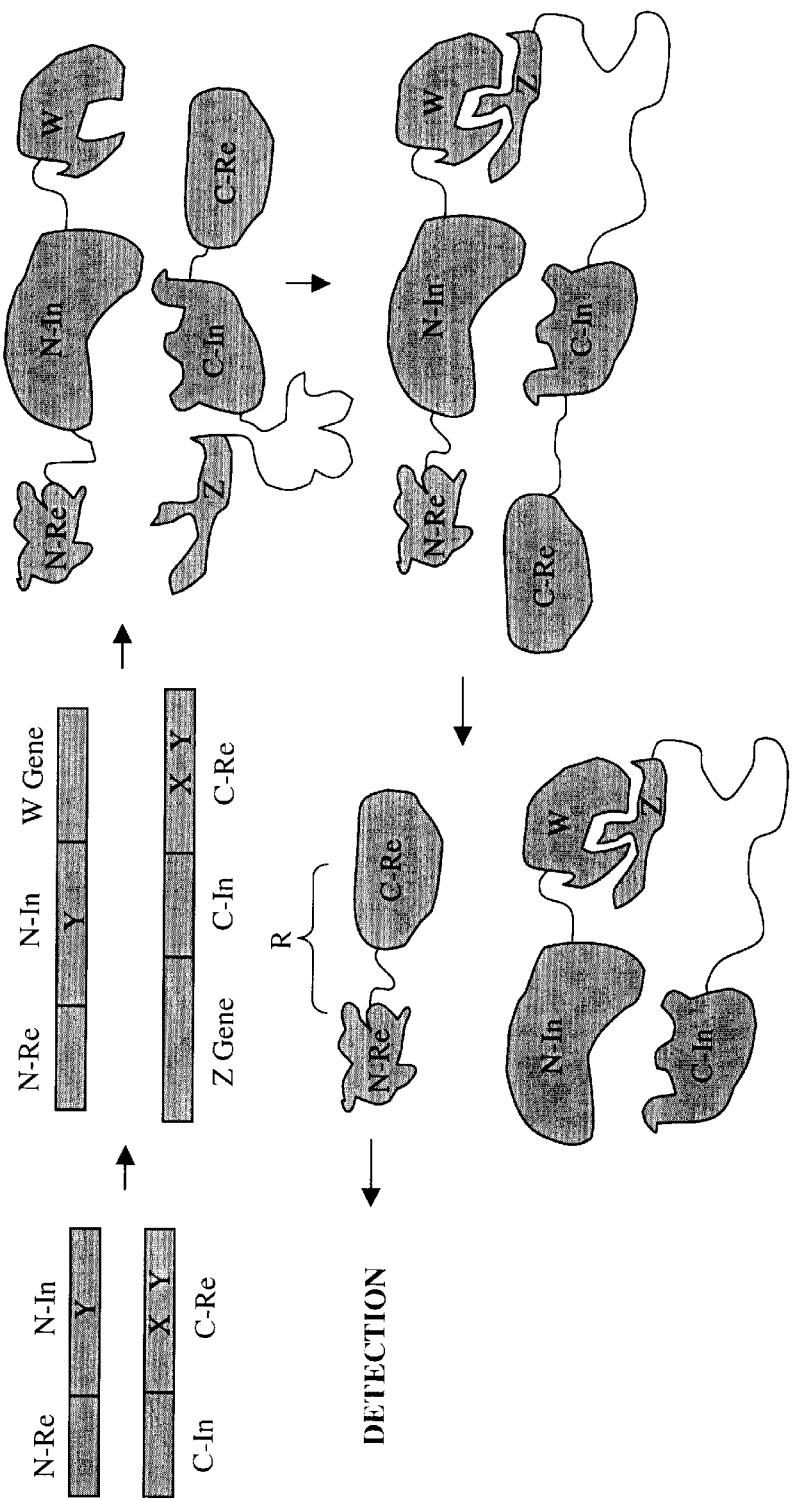
Figure 2B  Verifying That the Selected Non-interacting N-intein & C-intein Are Capable of Mediating Protein Splicing Figure 6 Intein-Based Multi-Hybrid System

YEAST TWO-HYBRID SYSTEM AND USE THEREOF

RELATED APPLICATIONS

This application claims priority from U.S. Provisional Application No. 60/259,759 filed on Jan. 4, 2001, which is incorporated herein by reference in its entirety.

FIELD OF THE INVENTION

The present invention generally relates to methods for detecting protein-protein interactions, and particularly to two-hybrid systems for detecting protein-protein interactions.

BACKGROUND OF THE INVENTION

There has been much interest in protein-protein interactions in the field of proteomics. A number of biochemical approaches have been used to identify interacting proteins. These approaches generally employ the affinities between interacting proteins to isolate proteins in a bound state. Examples of such methods include coimmunoprecipitation and copurification, optionally combined with cross-linking to stabilize the binding. Identities of the isolated protein interacting partners can be characterized by, e.g., mass spectrometry. See e.g., Rout et al., *J. Cell. Biol.*, 148:635–651 (2000); Houry et al., *Nature*, 402:147–154 (1999); Winter et al., *Curr. Biol.*, 7:517–529 (1997). A popular approach useful in large-scale screening is the phage display method, in which filamentous bacteriophage particles are made by recombinant DNA technologies to express a peptide or protein of interest fused to a capsid or coat protein of the bacteriophage. A whole library of peptides or proteins of interest can be expressed and a bait protein can be used to screening the library to identify peptides or proteins capable of binding to the bait protein. See e.g., U.S. Pat. Nos. 5,223,409; 5,403,484; 5,571,698; and 5,837,500. Notably, the phage display method only identifies those proteins capable of interacting in an in vitro environment, while the coimmunoprecipitation and copurification methods are not amenable to high throughput screening.

The yeast two-hybrid system is a genetic method that overcomes certain shortcomings of the above approaches. The yeast two-hybrid system has proven to be a powerful method for the discovery of specific protein interactions in vivo. See generally, Bartel and Fields, eds., *The Yeast Two-Hybrid System*, Oxford University Press, New York, N.Y., 1997. The yeast two-hybrid technique is based on the fact that the DNA-binding domain and the transcriptional activation domain of a transcriptional activator contained in different fusion proteins can still activate gene transcription when they are brought into proximity to each other. As shown in FIG. 1, in a yeast two-hybrid system, two fusion proteins are expressed in yeast cells. One has a DNA-binding domain of a transcriptional activator fused to a test protein. The other, on the other hand, includes a transcriptional activating domain of the transcriptional activator fused to another test protein. If the two test proteins interact with each other in vivo, the two domains of the transcriptional activator are brought together reconstituting the transcriptional activator and activating a reporter gene controlled by the transcriptional activator. See, e.g., U.S. Pat. No. 5,283,173.

Because of its simplicity, efficiency and reliability, the yeast two-hybrid system has gained tremendous popularity in many areas of research. Numerous protein-protein interactions have been identified using the yeast two-hybrid system. The identified proteins have contributed significantly to the understanding of many signal transduction pathways and other biological processes. For example, the yeast two-hybrid system has been successfully employed in identifying a large number of novel cell cycle regulators that are important in complex cell cycle regulations. Using known proteins that are important in cell cycle regulation as baits, other proteins involved in cell cycle control were identified by virtue of their ability to interact with the baits. See generally, Hannon et al., in *The Yeast Two-Hybrid System*, Bartel and Fields, eds., pages 183–196, Oxford University Press, New York, N.Y., 1997. Examples of cell cycle regulators identified by the yeast two-hybrid system include CDK4/CDK6 inhibitors (e.g., p16, p15, p18 and p19), Rb family members (e.g., p130), Rb phosphatase (e.g., PP1-$\alpha$2), Rb-binding transcription factors (e.g., E2F-4 and E2F-5), General CDK inhibitors (e.g., p21 and p27), CAK cyclin (e.g., cyclin H), and CDK Thr161 phosphatase (e.g., KAP and CDI1). See id. "[T]he two-hybrid approach promises to be a useful tool in our ongoing quest for new pieces of the cell cycle puzzle." See id at page 193. In another example, the yeast two-hybrid system proved to be a powerful approach in analyzing the yeast pheromone response pathway, a complex multistep signal transduction process in haploid yeast cell mating. See generally, Sprague et al., in *The Yeast Two-Hybrid System*, Bartel and Fields, eds., pages 173–182, Oxford University Press, New York, N.Y., 1997. As described in Sprague, various genes were isolated from mutant yeast strains having altered pheromone response patterns. However, it was not clear how the proteins encoded by these genes function in the pheromone response pathway. The yeast two-hybrid system was utilized to test such proteins and mutant forms thereof for their ability to interact with each other. As a result, new insights and better understandings of the complex process were achieved. See id.

The classic yeast two-hybrid system depends on gene activation in yeast nucleus and has generally required that specific protein-protein interactions between fusion proteins occur within the nucleus of yeast cells. Thus, although the conventional yeast two-hybrid system has been used successfully in the discovery of numerous protein interactions, its usefulness may be limited when it is used in detecting those protein-protein interactions that require non-nuclear environment. For example, many cell surface proteins and their ligands contain disulfide bonds, which can be disrupted under the intracellular reducing conditions. Additionally, posttranslational protein modifications, particularly glycosylation, typically would preclude the nuclear localization of the modified proteins.

Cytosolic and cell surface protein-protein interactions play major roles in normal cellular functions and biological responses. In particular, many cytosolic and cell surface protein-protein interactions are involved in disease pathways. For example, attacks by pathogens such as viruses and bacteria on mammalian cells typically begin with interactions between viral or bacterial proteins and mammalian cell surface proteins. Therefore, there is a need in the art for improved methods that can be used to efficiently detect cytosolic and cell surface protein-protein interactions.

SUMMARY OF THE INVENTION

This invention provides a versatile and sensitive yeast-based assay system for detecting protein-protein interactions that circumvents the above-described limitations inherent in prior art methods. Particularly, the present invention utilizes the so-called inteins, which are peptide sequences capable of directing protein trans-splicing. An intein is an intervening protein sequence in a protein precursor that is excised from the protein precursor during protein splicing. Protein splicing results in the concomitant ligation of the flanking protein fragments, i.e., the exteins, with a native peptide bond, thus forming a mature extein protein and the free intein. It is now known that inteins incorporated into non-native precursors can also cause protein-splicing and excision of the inteins. In addition, an N-terminal intein fragment in a fusion protein and a C-terminal intein fragment in another fusion protein, when brought into contact with each other, can bring about trans-splicing between the two fusion proteins. Thus, in accordance with the present invention, two-hybrid fusion proteins are provided in yeast cells. One has a first test polypeptide and an N-terminal intein fragment or N-intein, and the other has a second test polypeptide and a C-terminal intein fragment or C-intein. In addition, one or both fusion proteins may have a reporter that undergoes detectable changes upon trans-splicing of the fusion proteins. If the first and second test polypeptides interact with each other, thus bringing the N-intein and C-intein to close proximity, protein trans-splicing takes place. As a result, the fusion proteins are spliced, causing detectable changes in the reporter. Thus, by detecting the changes in the reporter, interactions between two test polypeptides can be determined.

Unlike the traditional two-hybrid systems, the intein-based yeast two-hybrid system of the present invention does not require that the interacting proteins be transported into cell nucleus. Thus, the system is useful in determining protein-protein interactions that require a specific cellular environment. For example, the system can be employed to detect interactions between nuclear proteins, between cytosolic proteins, and between membrane or extracellular proteins.

Additionally, protein trans-splicing mediated by the N-intein and C-intein is independent of other cellular factors and does not require the action of additional proteins such as proteases. This makes the assay system of the present invention more reliable and easier to perform as compared to the assay methods known in the art for detecting protein-protein interactions.

Another distinct feature of the intein-based yeast assay is that the detection of protein-protein interaction is based on the occurrence of protein trans-splicing events, which typically are associated with protein cleavage and result in new protein structures and functions. Thus, the intein-based assay is well-suited to exploit the numerous direct and indirect methods available in the art for detecting changes in protein structures and functions. Because the intein-based assay can accommodate these numerous detection methods, there is great flexibility in choosing methods that are optimal for a particular condition.

Furthermore, in contrast to prokaryotes-based systems, the intein-based yeast two-hybrid system of the present invention utilizes eukaryotic yeast cells in which mammalian proteins, particularly human proteins, can be easily expressed with high fidelity and efficiency. In addition, the cell compartmental localization of mammalian proteins or fusion proteins containing mammalian components is more likely to resemble their native state in yeast cell than in bacteria. Thus, the yeast-based system is a much more reliable and versatile system. It is amenable to protein-protein interactions that are not detectable by prokaryotes-based systems while producing less false positive protein-protein interactions that do not naturally occur.

Briefly, two fusion proteins are expressed in a yeast cell and allowed to interact with each other. One of the two fusion proteins includes an N-intein and a first test polypeptide, and the other fusion protein includes a C-intein and a second test polypeptide. One or both of the two fusion proteins have an inactive reporter capable of being converted to an active reporter upon trans-splicing through the N-intein and the C-intein. The change in the active reporter level is determined. An increase in the amount of the active reporter would indicate that the first and second test polypeptides interact with each other through, e.g., binding affinity, to result in the trans-splicing of the two fusion proteins mediated by the N-intein and the C-intein. Preferably, the N-intein and C-intein are not associated with each other and do not exhibit any significant binding affinity to each other. Nor do they associate with or bind to the inactive reporter or test polypeptides in the fusion proteins.

In one embodiment, the inactive reporter can be a polypeptide linked to one of the fusion proteins, and is cleaved off into a free form from the fusion protein upon protein trans-splicing. The reporter polypeptide can be selected and the fusion proteins can be designed such that the precursor form of the polypeptide is inactive while the free reporter released from the fusion protein is active, i.e., is detectable directly or indirectly.

In another embodiment, one of the two fusion proteins has a nonfunctional portion of a reporter polypeptide linked to the N-terminus of the N-intein. The other fusion protein comprises a distinct but similarly nonfunctional portion of the same reporter polypeptide linked to the C-terminus of the C-intein. Upon trans-splicing between the two fusion proteins through the N- and C-inteins, the two inactive reporter polypeptides are ligated together with a peptide bond, thereby forming an active reporter protein, which is detectable directly or indirectly.

To express the above-described fusion proteins, chimeric genes encoding the fusion proteins are introduced into a host cell. The amount of the active reporter protein in the host cell is then determined. In a preferred embodiment, a first chimeric gene encoding one of the two fusion proteins is expressed in a haploid Saccharomyces cell of a mating type a and a second chimeric gene encoding the other fusion protein is expressed in a haploid Saccharomyces cell of mating type α. The two cells are mated to form a diploid cell, and any change in the amount of the active reporter protein in the diploid is then determined.

In a specific embodiment, the expression of one or more of the chimeric genes can be made inducible, e.g., by placing the genes under the control of an inducible promoter, such that one or more of the fusion proteins are produced when the host cell is subject to a predetermined condition.

In addition, the assay can also be conducted in the presence of a third polypeptide. In this manner, the interaction between the first and second test polypeptides can be detected if the interaction requires the presence of the third polypeptide. The third polypeptide may be a protein having affinity to either the first or second test polypeptides or both. Alternatively, the third polypeptide can modify one or both test polypeptides, e.g., by phosphorylation, glycosylation, and the like.

The techniques used for monitoring the occurrence of protein trans-splicing events and detecting an active reporter will depend on the inactive reporter used and the active reporter derived therefrom. The system of the present invention can be designed such that an active reporter can be detected based on changes in protein sizes or other properties, or activation of certain protein functions. For example, detection of an active reporter can be based on cell viability assays, color assays, and the like.

In accordance with another aspect of the present invention, a kit for detecting protein-protein interactions is provided, which includes a first expression vector containing a first chimeric gene having operably linked in the same open reading frame: (a) a sequence encoding a first inactive reporter polypeptide; (b) a coding sequence for N-intein; and (c) a first multiple cloning site. The kit also includes a second expression vector containing a second chimeric gene having operably linked in the same open reading frame: (a) a second multiple cloning site; (b) a coding sequencing for C-intein; (c) a sequence encoding a second inactive reporter polypeptide, wherein ligation between the C-terminus of said first inactive reporter polypeptide and the N-terminus of said second inactive reporter polypeptide forms an active reporter. Preferably the kit further includes a yeast cell deficient in the active reporter protein.

The foregoing and other advantages and features of the invention, and the manner in which the same are accomplished, will become more readily apparent upon consideration of the following detailed description of the invention taken in conjunction with the accompanying examples and drawings, which illustrate preferred or exemplary embodiments.

BRIEF DESCRIPTION OF THE DRAWINGS

FIG. 2A illustrates a genetic selection process for selecting N-inteins and C-inteins that do not interact with each other;

FIG. 2B shows a process for verifying that the selected non-interacting N-intein and C-intein are capable of mediating protein trans-splicing;

DETAILED DESCRIPTION OF THE INVENTION

Figure 1:
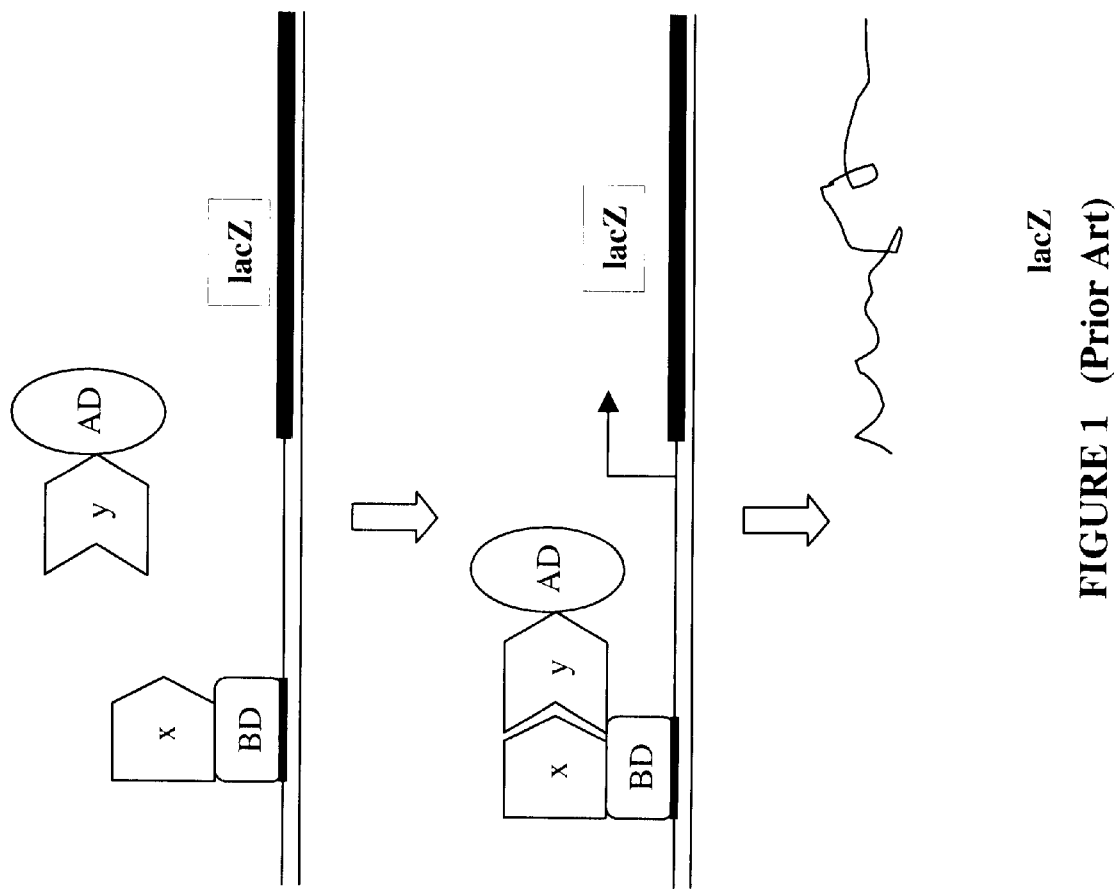
FIG. 1 is an illustration of the classic yeast two-hybrid system known in the art.

As used herein, the terms "polypeptide," "protein," and "peptide" are used interchangeably to refer to amino acid chains in which the amino acid residues are linked by covalent peptide bonds. The amino acid chains can be of any length of at least two amino acids, including full-length proteins. Unless otherwise specified, the terms "polypeptide," "protein," and "peptide" also encompass various modified forms thereof, including but not limited to glycosylated forms, phosphorylated forms, etc.

The term "test polypeptide" means a chemical compound, preferably an organic compound, to be tested in the present invention to determine its ability to interact with another chemical compound. Test polypeptides may include various forms of organic compounds, or combinations or conjugates thereof. In one embodiment, the test polypeptides preferably are polypeptides, in which case the test polypeptides are termed "test polypeptides" or "test proteins."

The term "fusion protein" refers to a non-naturally occurring hybrid or chimeric protein having two or more distinct portions covalently linked together, each portion being or being derived from a specific molecule.

As used herein, the term "interacting" or "interaction" means that two domains or independent entities exhibit sufficient physical affinity to each other so as to bring the two "interacting" domains or entities physically close to each other. An extreme case of interaction is the formation of a chemical bond that results in continual, stable proximity of the two domains. Interactions that are based solely on physical affinities, although usually more dynamic than chemically bonded interactions, can be equally effective at co-localizing independent entities. Examples of physical affinities and chemical bonds include but are not limited to, forces caused by electrical charge differences, hydrophobicity, hydrogen bonds, van der Wals force, ionic force, covalent linkages, and combinations thereof. The state of proximity between the interacting domains or entities may be transient or permanent, reversible or irreversible. In any event, it is in contrast to and distinguishable from contact caused by natural random movement of two entities. Typically although not necessarily, an "interaction" is exhibited by the binding between the interacting domains or entities. Examples of interactions include specific interactions between antigen and antibody, ligand and receptor, and the like.

An "interaction" between two protein domains, fragments or complete proteins can be determined by a number of methods. For example, an interaction can be determined by functional assays such as the two-hybrid systems. Protein-protein interactions can also be determined by various biophysical and biochemical approaches based on the affinity binding between the two interacting partners. Such biochemical methods generally known in the art include, but are not limited to, protein affinity chromatography, affinity blotting, immunoprecipitation, and the like. The binding constant for two interacting proteins, which reflects the strength or quality of the interaction, can also be determined using methods known in the art. See Phizicky and Fields, *Microbiol. Rev.,* 59:94–123 (1995).

As used in the present disclosure, the term "reporter" means a molecule or a moiety or domain thereof that can be used as a marker for the determination of the occurrence of protein trans-splicing. An "inactive reporter" is a form of the reporter that is not detectable by a particular detection means, while an "active reporter" is a form of the reporter that is detectable by that detection means. It should be recognized that the terms "detectable" and "not detectable" are used herein in a relative sense. In essence, there should be a measurable or detectable change in the reporter, either quantitative or qualitative, upon intein-based trans-splicing. For purposes of the present discussion, "active reporters" include both reporters that are directly detectable and those reporters that are detectable indirectly. One example of an indirectly detectable active reporter is a transcription activator that can activate the transcription of a detectable gene and thus cause the synthesis of a detectable protein encoded by the detectable gene.

Many reporters are known in the art and the selection and application of any of those reporters to the present invention should be apparent to a skilled artisan apprised of the present disclosure. Examples of reporters suitable for use in a yeast system or other systems include, but are not limited to: β-galactosidase (β-Gal) encoded by the LacZ gene which converts white X-Gal into a product with a blue color; the product of the CYH2 gene, which confers sensitivity to cycloheximide (CYH); proteins encoded by the auxotrophic genes URA3, HIS3, LEU2, and TRP1; and green fluorescent protein (GFP), which can be sorted by flow-activated cell sorting (FACS). See Cubitt et al., *Trends Biochem. Sci.*, 20:448–455 (1995).

Typically, an inactive reporter can be converted to an active reporter upon trans-splicing in the method of this invention. For example, a molecule when fused to a construct of the present invention may not be detectable and thus is referred to as "an inactive reporter." The fused form may be released from the fusion protein into a free form of the molecule that is detectable. This detectable free form is referred to as an "active reporter," which is in contrast to the "inactive" undetectable bound form of the reporter. In another example, two inactive reporters are fused to an N-intein and a C-intein, respectively, and upon trans-splicing, the two inactive reporters are ligated together forming a detectable active reporter. For this purpose, fragments of an active reporter that are not detectable can also be referred to "inactive reporter." Thus, an N-terminal fragment of a reporter protein is fused to an N-intein and a C-terminal fragment of the reporter protein is fused to a C-intein. Upon protein trans-splicing mediated by the N- and C-intein, the N-terminal and C-terminal fragments can be ligated, thereby forming a full-length detectable active reporter protein.

As is known in art, inteins are intervening protein sequences in protein precursors which are exercised out, or removed, from the protein precursors during protein splicing. The protein sequences flanking inteins are called exteins. The excision of an intein is associated with the concomitant ligation of the N-extein (the protein sequence to the N-terminus of the intein) and the C-extein (the protein sequence to the C-terminus of the intein) through a native peptide bond thus forming a mature extein protein and a free intein. See Perler et al., *Nucleic Acids Res.*, 22:1125–1127 (1994). The entire protein splicing process is autocatalyzed by the intein and is believed to be independent of specific host cell factors. Indeed, intein-based protein splicing has been shown to occur in vitro as well as in heterologous organisms. See Perler et al., *Cell*, 92:1–4 (1998). Intein-based protein splicing has also been shown to be independent of the native flanking exteins. Hybrid protein sequences containing inteins fused to non-native polypetide sequences are able to undergo protein splicing to excise the inteins and ligate the flanking polypeptide sequences. See e.g., Evans et al., *J. Biol. Chem.*, 274:3923–3926 (1999); Evans et al., *J. Biol. Chem.*, 275:9091–9094 (2000).

Certain amino acid sequences within an intein sequence are irrelevant to protein splicing. Based on sequence comparison and structural analysis, it is now known that the residues responsible for splicing are the intein N-terminal 100 amino acids, approximately, and the intein C-terminal 50 amino acids, approximately. See e.g., Duan et al., *Cell*, 89:555–564(1997), Hall et al., *Cell*, 91:85–97 (1997); Klabunde et al., *Nature Struct. Biol.* 5:31–36 (1998). Indeed, a functional mini-intein can be produced by deleting the centrally located irrelevant amino acid sequence leaving the N-terminal sequence of about 100 amino acids fused directly to the C-terminal sequence of about 50 amino acids. See e.g., Wu et al., *Biochim. Biophys. Acta.*, 1387:422–32 (1998). In addition, inteins have been identified that can mediate trans-splicing even when the N-terminal intein sequence and the C-terminal intein sequence are in different proteins. See id.; see also, Shingledecker et al., *Gene*, 207:187–195 (1998); Evans et al., *J. Biol. Chem.*, 274:3923–3926 (1999); Evans et al., *J. Biol. Chem.*, 275:9091–9094 (2000).

The present invention utilizes the trans-splicing capability of inteins to provide a method for detecting protein-protein interactions in yeast. Thus, in accordance with the present invention, two fusion proteins are provided in a yeast cell: one has a first test polypeptide and an N-intein, and the other has a second test polypeptide and a C-intein. In addition, one or both fusion proteins have a reporter that undergoes detectable changes upon intein-mediated trans-splicing of the fusion proteins. If the first and second test polypeptides interact with each other and bring the N-intein and C-intein into close proximity to each other, protein trans-splicing takes place. As a result, the fusion proteins are trans-spliced and/or re-ligated causing detectable changes in the reporter. By detecting the changes in the reporter, the interaction between two test polypeptides can be determined.

As used herein, the terms "N-intein" and "C-intein" refer to an N-terminal and a C-terminal portion of an intein, respectively. An N-intein itself alone cannot direct protein splicing, and likewise, a C-intein itself alone is incapable of catalyzing protein splicing. However, when an N-intein and a C-intein are placed in close proximity, they are capable of acting in concert to catalyze protein trans-splicing. Conserved intein motifs have been identified in many inteins. Typically, an intein includes an N-terminal splicing region having sequence motifs designated A, $N_2$, B, and $N_4$, an endonuclease or linker domain region having sequence motifs designated C, D, E, and H, and a C-terminal splicing region having sequence motifs designated F and G. See Pietrokovski, *Protein Sci.*, 3:2340–2350 (1994); Pietrokovski, *Protein Sci.*, 7:64–71 (1998). Thus, in a specific embodiment, N-intein encompasses at least motifs A, $N_2$, B, and $N_4$, while C-intein includes at least motifs F and G. Typically, "N-intein" is an amino acid sequence matching the N-terminal sequence of about 90 to 110 amino acids of an intein, while "C-intein" is an amino acid sequence matching the C-terminal sequence of about 30 to 50 amino acids of an intein. A skilled artisan will recognize that optimal sequences of N-inteins and C-inteins can be determined by routine trial and error experiments. In addition, it should be understood that the terms "N-intein" and "C-intein" also encompass non-native or modified amino acid sequences that are derived from an N-terminal or C-terminal portion of an intein, respectively, e.g., modified or mutein forms containing amino acid insertions, deletions, or substitutions.

Protein precursors containing inteins have been found in all three life domains: archaea, bacteria, and eucarya. A large number of inteins exist in bacteria and a few found in yeast. See Perler et al., *Nucleic Acids Res.*, 28:1 344–5 (2000); see also *InBase, the New England Intein Database*. The N-intein and C-intein used in the fusion proteins of the present invention can be selected according to the naturally occurring intein sequences. Alternatively, the naturally occurring intein sequences can be modified by deleting, inserting, or substituting amino acids to generate desirable properties in the N- and C-intein.

Some naturally occurring native N-inteins and C-inteins are known to interact with each other. This may cause undesireable background and could yield a high frequency of false positives. To minimize the background and increase the assay sensitivity in the present invention, it is preferred to use an N-intein and a C-intein that do not substantially interact with each other. That is, they do not exhibit sufficient physical affinity to each other or form chemical bonds between them so as to bring them physically close to each other to cause substantial protein trans-splicing. Such non-interaction will be operationally defined as an inability of an N-intein/C-intein pair to yield an active reporter when fused to test polypeptides known to have no affinity for one another.

If the N-intein and C-intein have relatively high affinity to each other, the N-intein and C-intein can be mutated to minimize their interaction. Alternatively, as will be described in detail below, competitive inhibitors of the reporters can be applied to minimize background detection signals. In this way, the detection signal from the active reporter produced by the interaction between the test proteins will be sufficiently greater than the background detection signal such that the interaction between the test proteins can be distinguished from the background interaction between the N-intein and C-intein.

Various trans-splicing assays may be used in combination with recombinant mutagenesis techniques to generate an N-intein and a C-intein that do not interact with each other and yet are capable of catalyzing protein trans-splicing when brought to proximity to each other. Conveniently, a genetic selection assay can be employed. For example, as shown in FIG. 2A, two chimeric genes can be prepared using standard recombinant DNA technologies. One chimeric gene encodes a fusion protein containing the N-terminal fragment of a reporter protein fused, at its C-terminus, to the N-terminus of an N-intein. The other chimeric gene encodes a fusion protein having a C-intein fused, at its C-terminus, to the N-terminus of the C-terminal fragment of a reporter protein. The N- and C-terminal fragments of the reporter protein should not interact with each other or with N- or C-intein. They can be in any length so long as an active reporter protein can be generated when they are ligated together through protein trans-splicing mediated by the N- and C-intein. The genetic selection assay can be performed in any suitable host cells, preferably conducted in yeast cells. The two chimeric genes are introduced to a host cell for the expression of the two fusion proteins. Alternatively, in the case of yeast cells, they can be introduced into two yeast cells having different mating types, which are subsequently mated. If the N-intein and C-intein thus expressed interact with each other, an active reporter will be detectable in the host cell. To obtain N-inteins and C-inteins that do not interact with each other, the DNA coding regions for the N-intein and C-intein are mutated using standard mutagenesis techniques to create changes in the amino acid sequences of the N- and C-intein. The thus generated mutant chimeric genes are then introduced into host cells for the genetic selection assay described above. If the active reporter is cytotoxic or cytostatic, one can select for those yeast cells that express mutant N- and C-inteins that fail to interact spontaneously. Finally, both the N- and C-extein fusion proteins can be C-terminally tagged with an epitope to allow immunologic confirmation of expression of the non-interacting intein mutants. In this manner, random mutations can be caused in the N- and C-intein and those mutant N-inteins and C-inteins that do not interact with each other are selected. See FIG. 2A.

Besides random mutagenesis, site-directed mutagenesis can also be used to change amino acid sequences in wild-type N- and C-inteins in predetermined manners. For example, amino acid sequences can be modified to create consensus sequences for phosphorylation by protein kinases or for glycosylation. Alternatively, certain amino acids in wild-type N- and C-intein sequences can also be chemically modified, e.g., by incorporating non-natural amino acids or by chemically linking certain moieties to amino acid side chains.

The selection of non-interacting N-intein and C-intein can also be done in an in vitro assay. For example, fusion proteins containing wild-type or mutated N- or C-inteins expressed from the above-described chimeric genes can be purified by standard chromatographic or affinity techniques or prepared in crude cell extracts. Fusion protein pairs (in which one contains an N-intein and the other contains a C-intein) are then mixed and incubated together in vitro under appropriate conditions to promote protein splicing as described below.

The thus selected N- and C-inteins are further tested for their ability to catalyze protein trans-splicing in a yeast cell. For this purpose, the selected chimeric genes containing desirable N- and C-intein coding sequences are further modified. FIG. 2B illustrates an example of this verification process. Essentially, a pair of new chimeric genes are constructed and introduced into a yeast cell for expressing a pair of fusion proteins. One chimeric gene encodes a fusion protein containing the above-described N-terminal fragment of a reporter protein fused, at its C-terminus, to the N-terminus of an N-intein, and a bait protein fused to the C-terminus of the N-intein. The other chimeric gene encodes a fusion protein having a C-intein fused, at its C-terminus, to the N-terminus of the above-described C-terminal fragment of a reporter protein, and a prey protein fused to the N-terminus of the C-intein. The bait protein and prey protein are known to interact with each other. Any pair of interacting proteins known in the art can be used for this purpose, such as the interacting pairs: FKBP12 and TGFβR1; FKBR12 and FRAP; thyroid hormone receptor α and nuclear core-pressor 1; Ras and Raf. See Huang and Schreiber, *Proc Natl Acad Sci USA*, 94:13396–401 (1997); Rossi et al., *Proc Natl Acad Sci USA*, 94:8405–10 (1997); Chen and Evans, *Nature*, 377:454–7 (1995); Pelletier et al., *Proc Natl Acad Sci USA*, 95:12141–6 (1998). After the new chimeric genes are expressed in a yeast cell to produce the fusion proteins, the active reporter is detected to determine whether trans-splicing has occurred. In this manner, N-inteins and C-inteins that do not interact with each other but are nevertheless capable of mediating protein trans-splicing in yeast cells when they are brought into proximity can be identified.

Thus, in accordance with present invention, two fusion proteins can be provided in yeast cells, one having an N-intein and a first test polypeptide and the other having a C-intein and a second test polypeptide. At least one of the two fusion proteins has an inactive reporter capable of being converted to an active reporter upon trans-splicing mediated by the N-intein and the C-intein. The two fusion proteins are then mixed and incubated together or allowed to contact with each other in other manners under appropriate conditions. Each of the two fusion proteins should be designed such that the interaction between the first and second test polypeptides can be determined by detecting or measuring the active reporter in the assay system.

Optionally, a control assay is conducted in parallel to the detection assay. Typically, in the control assay, the potential interaction between the two test polypeptides being assayed in the detection assay of this invention is pre-empted, eliminated or inhibited. For example, in one control assay, control fusion proteins are used, in which two known polypeptides that do not interact with each other are included in lieu of the first and second test polypeptides, respectively. Because the known polypeptides in the control fusion proteins do not interact with each other, any active reporter signal in the control assay is a background signal. Alternatively, in another control assay, the control fusion proteins do not contain the first or second test polypeptides. In other words, the control fusion proteins are different from those in a detection assay in that the control fusion proteins do not contain test polypeptides. Thus, any active reporter signal in the control assay would not be the result of interaction between the test polypeptides.

Preferably, a control assay utilizes the same two fusion proteins as those in a detection assay, which contain a first and a second test polypeptide, respectively. However, the control assay is conducted in the presence of an inhibitor that interferes with the interaction between the first and second test polypeptides in the fusion proteins. Typically, the inhibitor is an agent that interacts with one or both of the two test polypeptides in a manner such that the interaction between the two test polypeptides is disrupted, and as a result, the active reporter that would normally be formed upon interaction between the two test polypeptides is not produced. Conveniently, one of the two test polypeptides is used as an inhibitor. Such an agent should be in a free non-hybrid form or in a hybrid form that will not cause the formation of the active reporter upon an interaction between this hybrid form and the other test polypeptide in one of the two fusion proteins. For example, if the test polypeptide used as an inhibitor is a protein, it can be conveniently expressed from an expression vector containing a gene sequence encoding the protein.

The level of detectable active reporter in the control assay is compared to that in the detection assay. As a result, positive signals indicating specific interactions in the detection assay can be confirmed and distinguished from background signals inherent in the assay system. A control assay is especially useful when the N-intein and C-intein used in the fusion proteins can interact with each other.

A control assay can also be conducted simultaneously with the testing assay in the same host cell. In this case, the third and fourth fusion proteins described above should contain a second reporter different than that in the first and second fusion proteins such that the inability of the third and fourth fusion proteins to interact with each other can be demonstrated by detecting the presence or absence of an active form of the second reporter.

Alternatively, measures can be taken to reduce background signals. For example, in the case when cells of a His⁻ (His-deficient) yeast strain are used as host cells and the HIS3 gene product (imidazole glycerol phosphate dehydratase) is used as a reporter, the compound 3-amino-1,2,4-triazole (3-AT) can be added to the medium on which the yeast cells in the assay are grown. 3-aminotriazole (3-AT) specifically inhibits the HIS3-encoded enzyme imidazole glycerol phosphate dehydratase, which is required in yeast for the synthesis of the amino acid histidine. See Kishore et al., *Ann. Rev. Biochem.*, 57:627–663 (1988). As a result, a strong signal is required to confirm actual interaction between the test proteins. See Durfee et al., *Genes Dev.*, 7:555–569 (1993). Selection for progressively stronger reporter signaling can be achieved with progressively higher concentrations of 3-AT in the selection medium. Thus, with sufficiently high 3-AT concentrations, background growth on histidine-deficient media can be suppressed to allow use of an inherently "noisy" system.

The detection assay in accordance with the present invention is preferably conducted in a yeast cell. In this respect, fusion proteins can be recombinantly expressed in a host cell by introducing into the host cell chimeric genes encoding the fusion proteins. For this purpose, the expression vectors and host cells used in various two-hybrid systems developed in the art may be adapted and incorporated in the assays. Such two-hybrid systems are generally disclosed in U.S. Pat. Nos. 5,283,173; 5,525,490; 5,585,245; 5,637,463; 5,695,941; 5,733,726; 5,776,689; 5,885,779; 5,905,025; 6,037,136; 6,057,101; 6,114,111; and Bartel and Fields, eds., *The Yeast Two-Hybrid System*, Oxford University Press, New York, N.Y., 1997, all of which are incorporated herein by reference.

Typically, two chimeric genes are prepared encoding two fusion proteins as described above containing an N-intein and a C-intein, respectively. For the purpose of convenience, the two test polypeptides whose interaction is to be determined are referred to as "bait polypeptide" and "prey polypeptide," respectively. The chimeric genes encoding the fusion proteins containing the bait and prey polypeptides are termed "bait chimeric gene" and "prey chimeric gene," respectively. Typically, a "bait vector" and a "prey vector" are provided for the expression of a bait chimeric gene and a prey chimeric gene, respectively.

Many types of vectors can be used for the present invention. Methods for the construction of bait vectors and prey vectors should be apparent to skilled artisans in the art apprised of the present disclosure. See generally, *Current Protocols in Molecular Biology*, Vol. 2, Ed. Ausubel, et al., Greene Publish. Assoc. & Wiley Interscience, Ch. 13, 1988; Glover, *DNA Cloning*, Vol. II, IRL Press, Wash., D.C., Ch. 3, 1986; Bitter, et al., in *Methods in Enzymology* 153:516–544 (1987); *The Molecular Biology of the Yeast Saccharomyces*, Eds. Strathern et al., Cold Spring Harbor Press, Vols. I and II, 1982; and Rothstein in *DNA Cloning: A Practical Approach*, Vol. 11, Ed. D M Glover, IRL Press, Wash., D.C., 1986.

Generally, the bait and prey vectors may include a promoter operably linked to a chimeric gene for the transcription of the chimeric gene, an origin of DNA replication for the replication of the vectors in yeast cells and a replication origin for the amplification of the vectors in, e.g., *E. coli*, and selection marker(s) for selecting and maintaining only those yeast cells harboring the vectors. Additionally, the vectors preferably also contain inducible elements, which function to control the expression of the chimeric gene. Making the expression of the chimeric genes inducible and controllable is especially important in the event that the fusion proteins or components thereof are toxic to the host yeast cells. Other regulatory sequences such as transcriptional enhancer sequences and translation regulation sequences (e.g., Shine-Dalgarno sequence) can also be included. Termination sequences such as the bovine growth hormone, SV40, lacZ and AcMNPV polyhedral polyadenylation signals may also be operably linked to the chimeric gene. An epitope tag coding sequence for detection and/or purification of the fusion proteins can also be incorporated into the expression vectors. Examples of useful epitope tags include, but are not limited to, influenza virus hemagglutinin (HA), Simian Virus 5 (V5), polyhistidine (6×His), c-myc, lacZ, GST, and the like. Proteins with polyhistidine tags can be easily detected and/or purified with Ni affinity columns, while specific antibodies to many epitope tags are generally commercially available. Bait and prey vectors may also contain components that direct the expressed protein extracellularly or to a particular intracellular compartment. Signal peptides, nuclear localization sequences, endoplasmic reticulum retention signals, mitochondrial localization sequences, myristoylation signals, palmitoylation signals, and transmembrane sequences are example of optional vector components that can determine the destination of expressed proteins. The vectors can be introduced into host yeast cells by any techniques known in the art, e.g., by direct DNA transformation, microinjection, electroporation, viral infection, lipofection, gene gun, and the like. The bait and prey vectors can be maintained in yeast cells in an extrachromosomal state, i.e., as self-replicating plasmids or viruses. Alternatively, one or both vectors can be integrated into chromosomes of the host yeast cells by conventional techniques such as selection of stable cell lines or site-specific recombination.

In accordance with the present invention, the fusion proteins are expressed in a yeast expression system using yeasts such as *Saccharomyces cerevisiae, Hansenula polymorpha, Pichia pastoris*, and *Schizosaccharomyces pombe* as host cells. The expression of recombinant proteins in yeasts is a well developed area, and the techniques useful in this respect is disclosed in detail in *The Molecular Biology of the Yeast Saccharomyces*, Eds. Strathern et al., Vols. I and II, Cold Spring Harbor Press, 1982; Ausubel et al., *Current Protocols in Molecular Biology*, New York, Wiley, 1994; and Guthrie and Fink, *Guide to Yeast Genetics and Molecular Biology, in Methods in Enzymology*, Vol. 194, 1991, all of which are incorporated herein by reference. Sudbery, *Curr. Opin. Biotech.*, 7:517–524 (1996) reviews the success in the art in expressing recombinant proteins in various yeast species; the entire content and references cited therein are incorporated herein by reference. In addition, Bartel and Fields, eds., *The Yeast Two-Hybrid System*, Oxford University Press, New York, N.Y., 1997 contains extensive discussions of recombinant expression of fusion proteins in yeasts in connection with various yeast two-hybrid systems, and cites numerous relevant references. These and other methods known in the art can all be used for purposes of the present invention. The application of such methods to the present invention should be apparent to a skilled artisan apprised of the present disclosure.

Generally, each of the two chimeric genes (one having an N-intein coding sequence and the other having a C-intein coding sequence) of the present invention is included into a separate expression vector (bait vector and prey vector). Both vectors can be co-transformed into a single yeast host cell. As will be apparent to a skilled artisan, it is also possible to express both chimeric genes from a single vector. In a preferred embodiment, the bait vector and prey vector are introduced into two haploid yeast cells of opposite mating types, e.g., a-type and α-type, respectively. The two haploid cells can be mated at a desired time to form a diploid cell expressing both chimeric genes.

Generally, the bait and prey vectors for recombinant expression in yeasts include a yeast replication origin such as the 2$\mu$ origin or the ARSH4 sequence for the replication and maintenance of the vectors in yeast cells. Preferably, the vectors also have a bacteria origin of replication (e.g., ColE1) and a bacteria selection marker (e.g., amp$^R$ marker, i.e., bla gene). Optionally, the CEN6 centromeric sequence is included to control the replication of the vectors in yeast cells. Any constitutive or inducible promoters capable of driving gene transcription in yeast cells may be employed to control the expression of the chimeric genes. Such promoters are operably linked to the chimeric genes. Examples of suitable constitutive promoters include but are not limited to the yeast ADH1, PGK1, TEF2, GPD1, HIS3, and CYC1 promoters. Example of suitable inducible promoters include but are not limited to the yeast GAL1 (inducible by galactose), CUP1 (inducible by Cu$^{++}$), MEL1 (inducible by galactose), FUS1 (inducible by pheromone) promoters; the AOXIMOX promoter from *H. polymorpha* and *P. Pastoris* (repressed by glucose or ethanol and induced by methanol); chimeric promoters such as those that contain LexA operators (inducible by LexA-containing transcription factors); and the like. Inducible promoters are preferred when the fusion proteins encoded by the chimeric genes or the reporter proteins resulting from protein trans-splicing are toxic to the host cells. If it is desirable, certain transcription repressing sequences such as the upstream repressing sequence (URS) from SPO13 promoter can be operably linked to the promoter sequence, e.g., linked to the 5' end of the promoter region. Such upstream repressing sequences function to fine-tune the expression level of the chimeric genes.

Preferably, a transcriptional termination signal is operably linked to the chimeric genes in the vectors. Generally, transcriptional termination signal sequences derived from, e.g., the CYC1 and ADH1 genes can be used.

Additionally, it is preferred that the bait vector and prey vector contain one or more selectable markers for the selection and maintenance of only those yeast cells that harbor the chimeric genes of the present invention. Any selectable markers known in the art can be used for purposes of this invention so long as yeast cells expressing the chimeric gene(s) of the present invention can be positively identified or negatively selected. Examples of markers that can be positively identified are those based on color assays, including the lacZ gene which encodes β-galactosidase, the firefly luciferase gene, secreted alkaline phosphatase, horseradish peroxidase, the blue fluorescent protein (BFP), and the green fluorescent protein (GFP) gene (see Cubitt et al., *Trends Biochem. Sci.*, 20:448–455 (1995)). Other markers emitting fluorescence, chemiluminescence, UV absorption, infrared radiation, and the like can also be used. Among the markers that can be selected are auxotrophic markers that include, but are not limited to, URA3, HIS3, TRP1, LEU2, LYS2, ADE2, and the like. Typically, for purposes of auxotrophic selection, the yeast host cells transformed with bait vector and/or prey vector are cultured in a medium lacking a particular nutrient. Other selectable markers are not based on auxotrophies, but rather on resistance or sensitivity to an antibiotic or other xenobiotics. Examples include, but are not limited to, chloramphenicol acetyl transferase (CAT) gene, which confers resistance to chloramphenicol; CAN1 gene, which encodes an arginine permease and thereby renders cells sensitive to canavanine (see Sikorski et al., *Meth. Enzymol.*, 194:302–318 (1991)); the bacterial kanamycin resistance gene (kan$^R$), which renders eucaryotic cells resistant to the aminoglycoside G418 (see Wach et al., *Yeast*, 10:1793–1808 (1994)); and CYH2 gene, which confers sensitivity to cycloheximide (see Sikorski et al., *Meth. Enzymol.*, 194:302–318 (1991)). In addition, the CUP1 gene, which encodes metallothionein and thereby confers resistance to copper, is also a suitable selection marker. Each of the above selection markers may be used alone or in combination. One or more selection markers can be included in a particular bait or prey vector. The bait vector and prey vector may have the same or different selection markers. In addition, the selection pressure can be placed on the transformed host cells either before or after mating the haploid yeast cells.

As will be apparent, the selection markers used should complement the host strains in which the bait and/or prey vectors are expressed. In other words, when a gene is used as a selection marker gene, a yeast strain lacking the selection marker gene (or having mutation in the corresponding gene) should be used as host cells. Numerous yeast strains or derivative strains corresponding to various selection markers are known in the art. Many of them have been developed specifically for certain yeast two-hybrid systems. The application and optional modification of such strains with respect to the present invention should be apparent to a skilled artisan apprised of the present disclosure. Methods for genetically manipulating yeast strains using genetic crossing or recombinant mutagenesis are well known in the art. See e.g., Rothstein, *Meth. Enzymol.,* 101:202–211 (1983). By way of example, the following yeast strains are well known in the art, and can be used in the present invention upon necessary modifications and adjustment:

L40 strain which has the genotype MATα his3Δ200 trp1-901 leu2-3,112 ade2 LYS2::(lexAop)4-HIS3 URA3::(lexAop)8-lacZ;

EGY48 strain which has the genotype MATα trp1 his3 ura3 6ops-LEU2; and

MaV103 strain which has the genotype MATα ura3-52 leu2-3,112 trp1-901 his3Δ200 ade2-101 gal4Δ gal80Δ SPAL10::URA3 GAL1::HIS3::lys2 (see Kumar et al., *J. Biol. Chem.* 272:13548–13554 (1997); Vidal et al., *Proc. Natl. Acad. Sci. USA,* 93:10315–10320 (1996)). Such strains are generally available in the research community, and can also be obtained by simple yeast genetic manipulation. See, e.g., *The Yeast Two-Hybrid System*, Bartel and Fields, eds., pages 173–182, Oxford University Press, New York, N.Y., 1997.

In addition, the following yeast strains are commercially available:

Y190 strain which is available from Clontech, Palo Alto, Calif. and has the genotype MATα gal4 gal80 his3Δ200 trp1-901 ade2-101 ura3-52 leu2-3, 112 URA3::GAL1-lacZ LYS2::GAL1-HIS3 cyh$^r$; and YRG-2 Strain which is available from Stratagene, La Jolla, Calif. and has the genotype MATα ura3-52 his3-200 ade2-101 lys2-801 trp1-901 leu2-3, 112 gal4-542 gal80-538 LYS2::GAL1-HIS3 URA3::GAL1/CYC1-lacZ.

In fact, different versions of vectors and host strains specially designed for yeast two-hybrid system analysis are available in kits from commercial vendors such as Clontech, Palo Alto, Calif. and Stratagene, La Jolla, Calif., all of which can be modified for use in the present invention.

As described above, each of the two fusion proteins should be designed such that the interaction between the first and second test polypeptides is determinable by detecting or measuring changes in the reporter in the assay system. It will be apparent from the above discussion, the reporter can be any molecules or moieties so long as changes in the reporter that are specifically associated with intein-mediated trans-splicing are detectable. It will be recognized that although the reporters and selection markers can be of similar types and used in a similar manner in the present invention, the reporters and selection markers should be carefully selected in a particular detection assay such that they are distinguishable from each other and do not interfere with each other's roles.

Conveniently, the occurrence of trans-splicing can be detected by detecting changes in the size of the reporter. For example, the sizes of the various components of the fusion proteins can be designed such that the "active reporter," which is generated when the "inactive reporter" is simply cleaved off from one of the fusion proteins or recombined with one or more other components of the fusion proteins, is distinguishable from its precursor(s) and other trans-splicing products based on size, i.e., molecular weight. The inactive reporter can be pre-labeled with, e.g., radioactive isotope or fluorescence or other detectable markers, and the active reporter can be detected in, e.g., gel electrophoresis either before or after purification. Purification can be based on specific affinity columns using an antigen-specific protein, e.g., light-chain immunoglobulin, heavy-chain immunoglobulin, avidin, streptavidin, protein A, and antigenic peptides. Conveniently, the commonly used and commercially available epitope tags may be used as size-based reporters. Such epitope tags include sequences derived from, e.g., influenza virus hemagglutinin (HA), Simian Virus 5 (V5), polyhistidine (6×His), c-myc, lacZ, GST, and the like. For example, proteins with polyhistidine tags can be easily detected and/or purified with Ni affinity columns. One advantage for using such epitope tags is that specific antibodies to many of these epitope tags are generally commercially available. Alternatively, an epitope-specific antibody specifically to the "active reporter" can be used to detect the level of the active reporter generated in the assay without purification.

In another embodiment, the fusion proteins are designed such that the active reporter produced during intein-mediated trans-splicing can be detected by a color-based assay. For example, when an N-terminal portion of the lacZ protein (β-galactosidase) is fused to the N-terminus of an N-intein in a fusion protein and a C-terminal portion of the lacZ protein is fused to the C-terminus of a C-intein in another fusion protein, protein trans-splicing will religate the N- and C-terminal portions of the lacZ protein to form a full-length complete and active lacZ protein. Thus, in the presence of a substrate for β-galactosidase (e.g., X-Gal, i.e., 5-bromo-4-chloro-3-indolyl-β-D-galactoside), the trans-splicing can be detected based on appearance of a blue color or by quantitative colorimetric assay. To produce the chimeric genes in this embodiment of the invention, the lacZ gene encoding β-galactosidase can be divided into a 5' portion and a 3' portion in any manner to encode an N-terminal portion and a C-terminal portion of the β-galactosidase. As discussed above, it may be advantageous to facilitate protein splicing if the first amino acid immediately following C-intein is cysteine, serine, or threonine. Thus, if at all possible, the division of the lacZ gene is made immediately before a genetic codon for cysteine, serine, or threonine such that the first amino acid in the C-terminal portion of β-galactosidase immediately following a C-intein in a fusion protein is one of the three preferred amino acids. Certain mutations may also be introduced into the lacZ gene to substitute a cysteine, serine or threonine for another amino acid, or for any other purposes, so long as the mutation does not adversely interfere with protein trans-splicing or the detection of the active reporter protein, i.e., β-galactosidase.

As will be apparent, many other reporters can be used in a similar manner in the present invention. Such other reporters include, for example, the green fluorescent protein (GFP), which can be detected by fluorescence assay and sorted by flow-activated cell sorting (FACS) (See Cubitt et al., *Trends Biochem. Sci.,* 20:448–455 (1995)), secreted alkaline phosphatase, horseradish peroxidase, the blue fluorescent protein (BFP), and luciferase photoproteins such as aequorin, obelin, mnemiopsin, and berovin (See U.S. Pat. No. 6,087,476, which is incorporated herein by reference).

Figure 4:
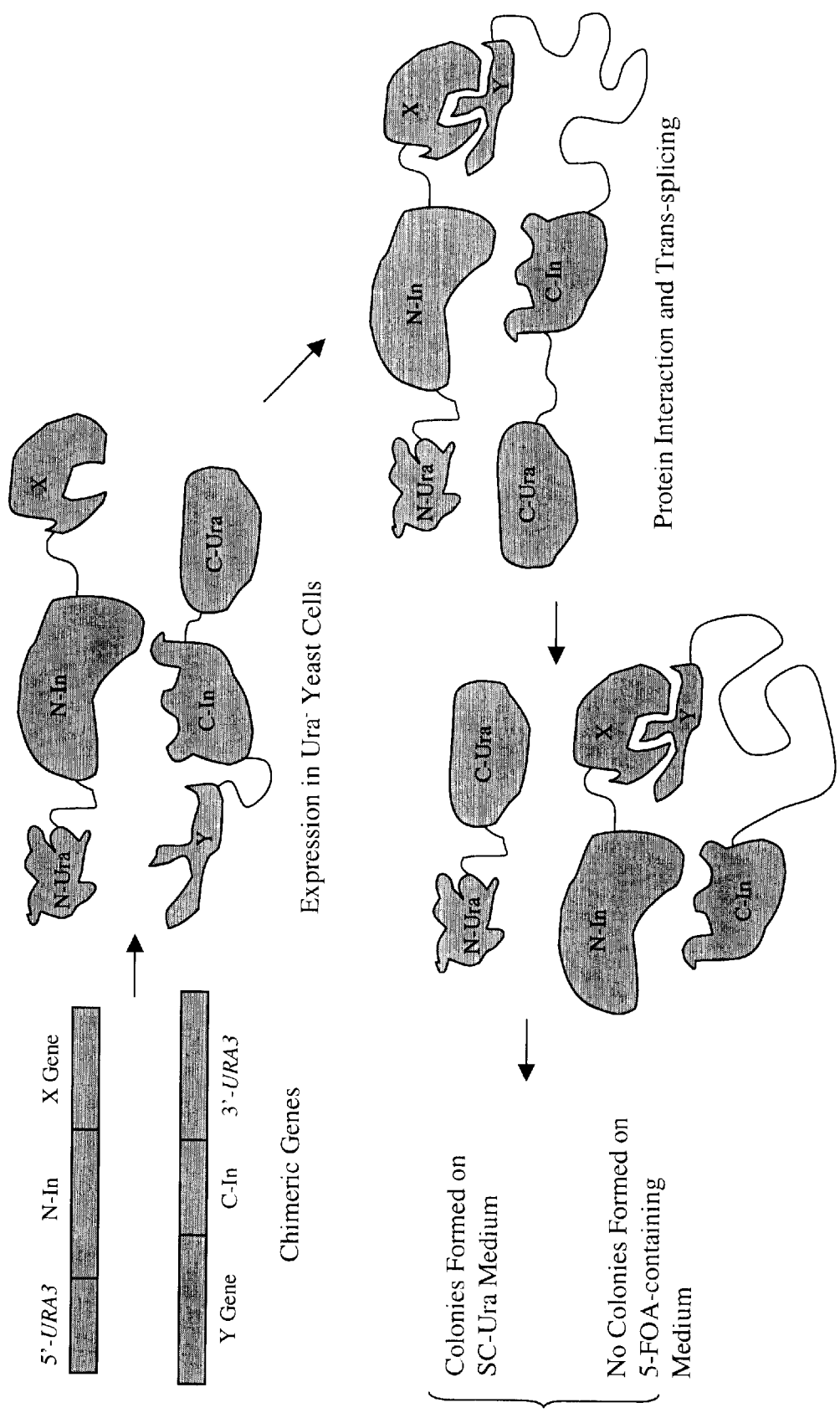
FIG. 4 is a drawing demonstrating the use of the protein encoded by the URA3 gene as a reporter protein in one embodiment of the present invention.

In another embodiment, an auxotrophic factor is used as a reporter in an in vivo assay in a host strain deficient in the auxotrophic factor. Thus, suitable auxotrophic reporter genes include, but not are limited to, URA3, HIS3, TRP1, LEU2, LYS2, ADE2, and the like. For example, yeast cells containing a mutant URA3 gene can be used as host cells (Ura⁻ phenotype) for the in vivo assay as illustrated in FIG. 4. Such cells lack URA3-encoded functional orotidine-5'-phosphate decarboxylase, an enzyme required by yeast cells for the biosynthesis of uracil. As a result, the cells are unable to grow on a medium lacking uracil. However, wild-type orotidine-5'-phosphate decarboxylase catalyzes the conversion of a non-toxic compound 5-fluoroorotic acid (5-FOA) to a toxic product, 5-fluorouracil. Thus, yeast cells containing a wild-type URA3 gene are sensitive to 5-FOA and cannot grow on a medium containing 5-FOA. Therefore, when an N-terminal portion of the URA3-encoded protein (orotidine-5'-phosphate decarboxylase) is fused to the N-terminus of an N-intein in a fusion protein and a C-terminal portion of the URA3-encoded protein is fused to the C-terminus of a C-intein in another fusion protein, protein trans-splicing initiated by interaction between the test proteins in the fusion proteins will result in ligation of the N- and C-terminal portions of the URA3-encoded protein, thereby forming a full-length, complete, and active orotidine-5'-phosphate decarboxylase. This enables the Ura⁻ Foa$^R$ yeast cells to grow on a uracil deficient medium (SC-Ura plates). However, such cells will not survive on a medium containing 5-FOA. Therefore, protein trans-splicing events and interactions between test proteins can be detected based on cell growth.

Additionally, antibiotic resistance reporters can also be employed in a similar manner. In this respect, host cells sensitive to a particular antibiotics is used. Antibiotics resistance reporters include, for example, chloramphenicol acetyl transferase (CAT) gene and the kan$^R$ gene, which confers resistance to G418 in eucaryotes and to kanamycin in prokaryotes.

Figure 5:
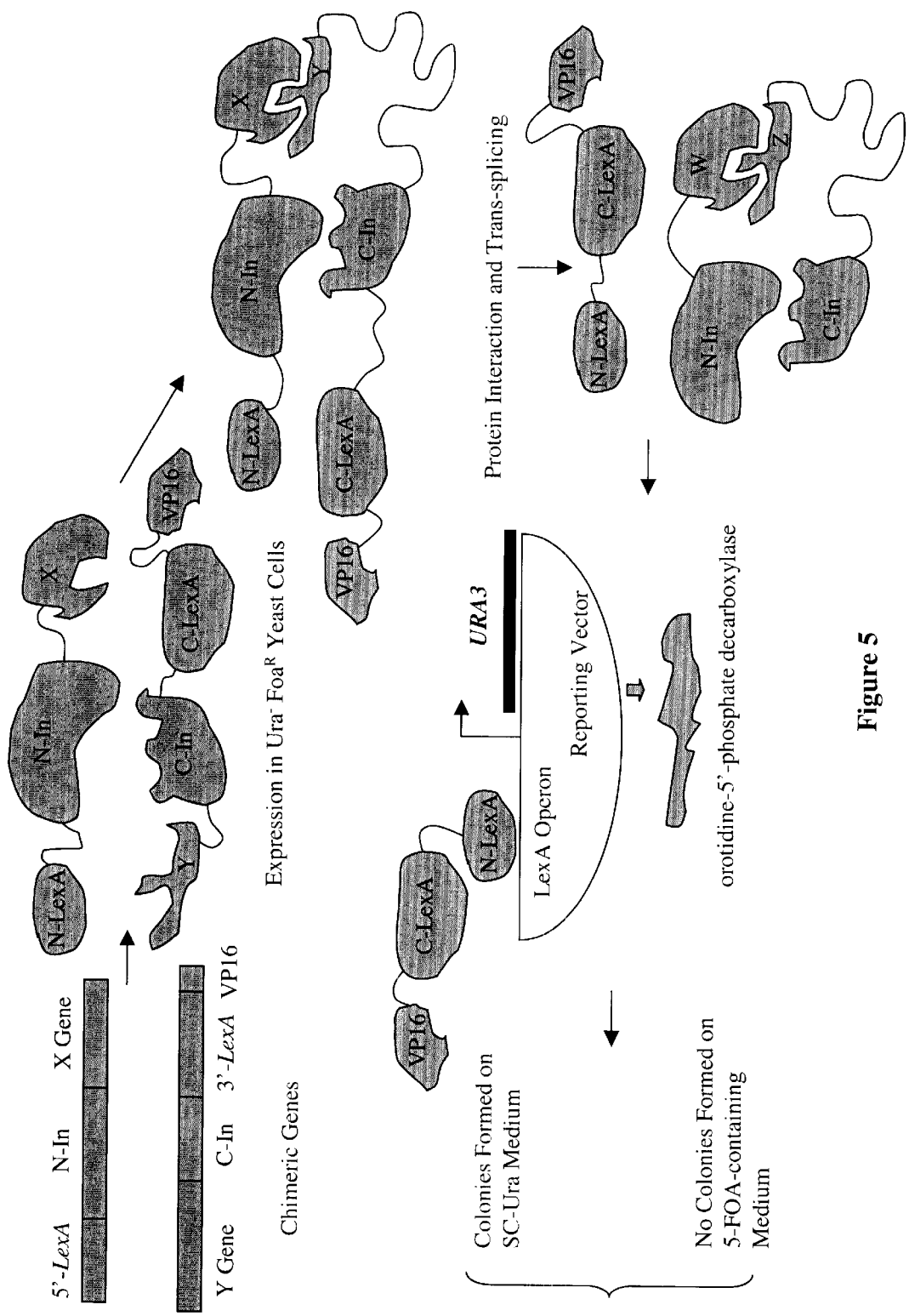
FIG. 5 shows an embodiment of the present invention in which a transcriptional activator is used as an active reporter which drives the expression of the selection marker gene URA3.

In yet another embodiment of the present invention, the fusion proteins are designed such that intein-mediated trans-splicing produces an active reporter that is a transcriptional activator or repressor capable of activating or repressing the expression of a detectable gene. Thus, the trans-splicing event will be detected based on the expression or suppression of the detectable gene. In this embodiment, a "reporting vector" containing the detectable gene operably linked to a transcriptional regulatory sequence is also introduced into the host cells. The above-described selection markers and reporter genes can all be used as the detectable gene for this purpose, so long as activation or suppression of the expression of the detectable gene is readily detectable. For example, as illustrated in FIG. 5, the URA3 gene can be used as a detectable gene in connection with either a transcriptional activator or suppressor. (An activator is shown in FIG. 5.) The URA3 gene is operably linked to a transcriptional regulatory sequence responsive to the transcriptional activator or suppressor. When the active reporter generated in trans-splicing is an activator, the yeast host cells (Ura⁻) grow on a uracil deficient (SC-Ura) medium and the interaction between the test proteins is detected based on yeast colony formation on the medium. Alternatively, when the active reporter generated in trans-splicing is a suppressor, the yeast host cells (Ura⁻) grow on a medium containing 5-fluoroorotic acid (5-FOA). In the absence of an interaction between the test proteins, the URA3 gene is expressed, and the 5-FOA is converted by the URA3 gene product into a toxic substance, which inhibits the growth of the host cells. In the presence of an interaction between the test proteins, a suppressor is generated and the URA3 gene expression is shut off. As a result, yeast colonies can be formed on a medium containing 5-FOA. The transcriptional regulatory sequence is designed such that the detectable gene is specifically responsive to the active reporter. Alternatively, a suitable detectable gene integrated in a chromosome of a host cell can also be used.

Suitable transcription activators include, but are not limited to, GAL4, GCN4, ARD1, the human estrogen receptor, *E. coli* LexA protein, herpes simplex virus VP16 (Triezenberg et al., *Genes Dev.* 2:718–729 (1988)), the *E. coli* B42 protein (acid blob, see Gyuris et al., *Cell*, 75:791–803 (1993)), NF-kB p65, and the like. In addition, hybrid transcriptional activators composed of a DNA binding domain from one transcriptional activator and an activation domain from another transcriptional activator are also useful. Examples of transcription suppressors include the Kruppel protein, the engrailed protein, the knirps protein, the paired protein and the even-skipped protein, all from Drosophila; the SIN3, GAL80, and TUP1 proteins, all from *Saccharomyces cerevisiae*; the tet repressor; the Egr-1, WT1, RARa, KRAB, verbA, YY1, ADE1B, E4B4, SCIP, kid-1, Znf2, and kox-1 proteins; and the like. The corresponding transcriptional elements specifically interacting with the transcriptional activators or repressors are well known in the art. See. e.g., Hanna-Rose and Hansen, *Trends. Genet.,* 12:229–234 (1996).

Thus, a transcriptional activator or repressor protein can be divided into an N-terminal portion and a C-terminal portion which are fused to the N-terminus of N-intein and C-terminus of C-intein, respectively. Upon protein trans-splicing, a full-length protein emerges as a functional transcriptional activator or repressor which subsequently activates or represses the expression of the detectable gene in the reporting vector. See FIG. 5. It is recognized that the interaction between the test proteins may bring the two portions of the transcriptional activator or suppressor together which may be sufficient to initiate or suppress the transcription of the detectable gene. In this respect, this specific embodiment of the present invention may be similar to the classic yeast two-hybrid system. However, unlike the classic transcription-based yeast two-hybrid system, it is possible in the present invention to produce an active transcriptional activator or suppressor that is authentic. Thus, the fusion proteins need not be transported into cell nucleus, since the transcriptional activator or suppressor, once formed during protein trans-splicing, is competent for translocation to the nucleus. Indeed, the method of the present invention enables use of mitochondrial transcription factors as reporters. Once formed by protein trans-splicing, such reporters can translocate to the mitochondria, where they can activate or suppress transcription of mitochondrially encoded, detectable genes.

The method of the present invention for detecting protein-protein interactions can also be used to screen an expression library or applied in the so-called "interaction mating." Methods for constructing activation domain or DNA binding domain fusion libraries and the use thereof in yeast two-hybrid system are well known in the art and are disclosed in e.g., Vojtek et al., in *The Yeast Two-Hybrid System*, Bartel and Fields, eds., pages 29–42, Oxford University Press, New York, N.Y., 1997; Zhu et al., in *The Yeast Two-Hybrid System*, Bartel and Fields, eds., pages 73–96, Oxford University Press, New York, N.Y., 1997. Interaction mating is disclosed in U.S. Pat. Nos. 6,057,101 and 6,083,693; and Finley and Brent, in *The Yeast Two-Hybrid System*, Bartel and Fields, eds., pages 197–214, Oxford University Press, New York, N.Y., 1997. The methods described in the above references can all be applied to the present invention upon appropriate modifications. By way of example, N-intein fusion libraries can be prepared using an expression vector containing a 5' portion of a reporter gene operably linked to the 5' end of N-intein coding sequence. Operably linked to the 3' end of the N-intein coding sequence is a multiple cloning site into which various random or predetermined (e.g., cDNAs) DNA sequences can be inserted in frame. The DNA library thus prepared can be transformed into appropriate yeast cells. In this yeast library, an array of fusion proteins can be expressed, with each fusion protein containing an N-terminal portion of the reporter protein fused to the N-terminus of the N-intein and a random or predetermined polypeptide fused to the C-terminus of the N-intein. Appropriate yeast cells expressing a fusion protein including a bait protein fused to the N-terminus of a C-intein and the C-terminal portion of the reporter protein fused to the C-terminus of the C-intein can be used to screen the yeast N-intein fusion library to identify prey proteins capable of interacting with the bait protein.

C-intein fusion libraries can also be established and used in "interaction mating" with the N-intein fusion libraries. In this way, interacting protein pairs can be identified and genes encoding such proteins are isolated.

In yet another embodiment of the detection method of the present invention, the detection assay is used to detect interactions between three or more agents in a trimeric or higher order complex. See U.S. Pat. No. 5,695,941; Chang et al., *Cell,* 79:131–141 (1994); Tirode et al., *J. Biol. Chem.,* 272:22995–22999 (1997); Van Criekinge et al., *Anal. Biochem.,* 263:62–66 (1998); and Pause et al., *Porc. Natl. Acad. Sci. USA,* 96:95339–538 (1999), all of which are incorporated herein by reference. Essentially, the above-described detection assay of this invention involving two fusion proteins is conducted in the presence of one or more other test polypeptides. In this manner, interactions between the two test polypeptides in the fusion proteins that require the participation of the other test polypeptides can be detected.

The other test polypeptides can be small molecule ligands that interact with the test polypeptides in the fusion proteins. Many protein-protein interactions require the presence of a small molecule ligand, which becomes an integral part of the assembly formed by the protein interactions. See Berlin, in *The Yeast Two-Hybrid System*, Bartel and Fields, eds., pages 259–272, Oxford University Press, New York, N.Y., 1997. For example, immune suppressants such as cyclosporin A (CsA), FK506, and rapamycin are known to bind with high affinity to immunophilins forming protein-drug complexes which, in turn, bind to specific target proteins to inhibit their activities. Classic yeast two-hybrid system has been employed successfully to isolate proteins interacting with the FKBP12/rapamycin complex. See, e.g., Chiu et al., *Proc. Nat. Acad. Sci. USA,* 91:12574–12578 (1994). A multi-hybrid assay in accordance with the present invention can be conducted both in vitro and in vivo. In an in vitro assay, the small molecule ligands are simply added to the above-described intein-based two-hybrid assay system of the present invention. In an in vivo assay, it is necessary that the small molecule ligands are taken-up by the host cells. While many host cells are able to take up various small molecule ligands, certain host cells can also be manipulated to increase the uptake of small molecule ligands. For example, yeast high uptake mutants such as erg6 mutant strains can facilitate the uptake of the test compounds by yeast cells. See Gaber et al. *Mol. Cell. Biol.,* 9:3447–3456 (1989).

Many protein interactions require the participation of other proteins. Thus, the other test polypeptides in the multi-hybrid assay of the present invention can also be proteins. Accordingly, genes encoding test proteins other than those in the intein-containing fusion proteins can be co-expressed in host cells with the chimeric genes as described above. Such additional genes may be incorporated into one of the bait or prey vector or the reporting vector. Alternatively, they can be expressed in separate vectors under control of a constitutive or inducible promoter.

Figure 6:
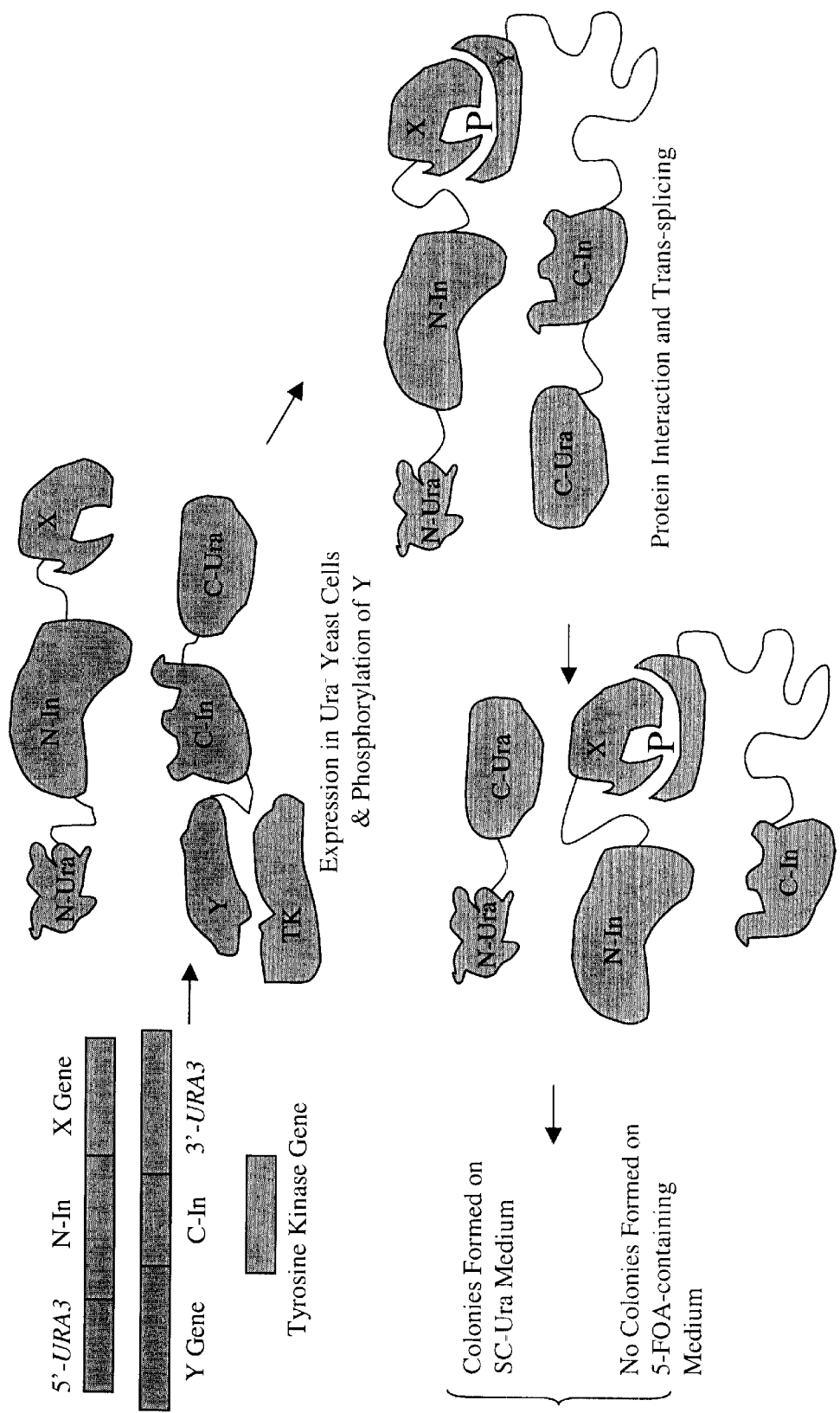
FIG. 6 is a diagram illustrating an embodiment of the present invention in which a modifying enzyme is expressed in a multi-hybrid system and interaction between the modified proteins is detected.
Figure 7:
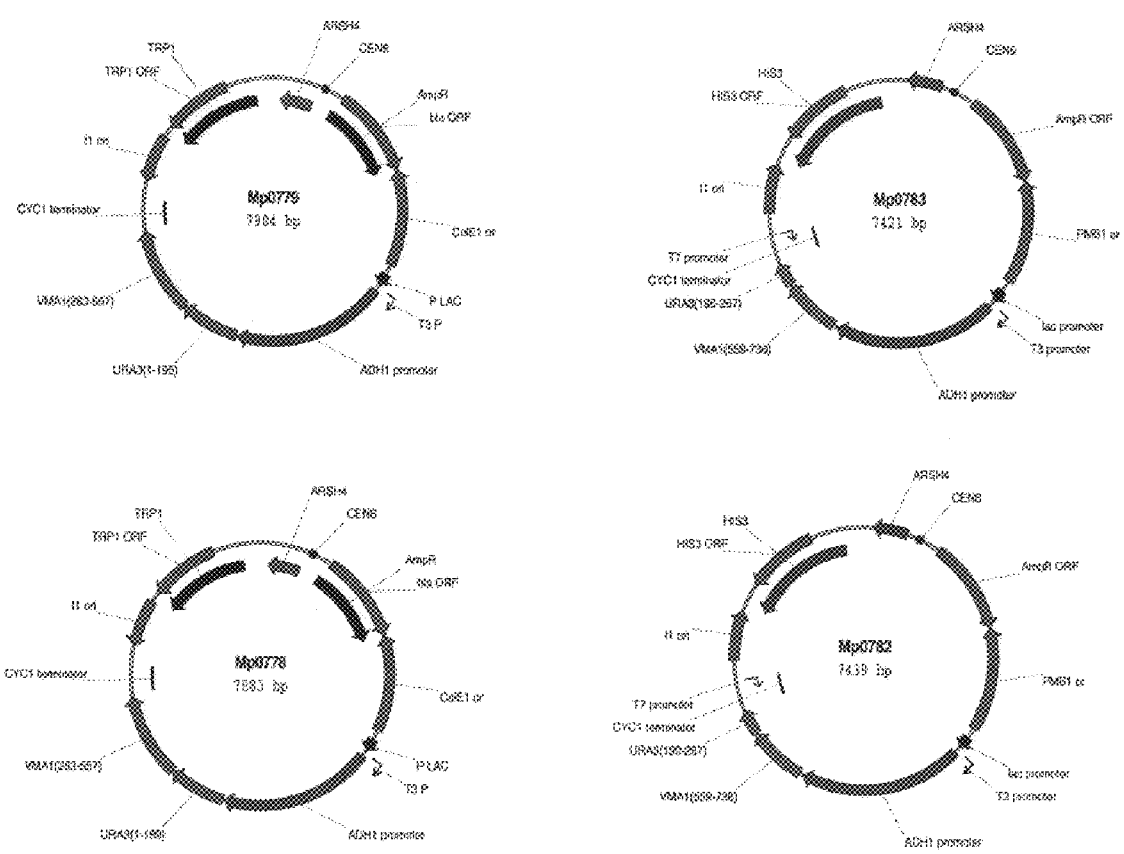
FIG. 7 illustrates four different vector constructs that allow expression of different fusion proteins used in the intein-based two-hybrid systems demonstrated in the Example.

In a specific embodiment, the additional test proteins are enzymes capable of post-translationally modifying at least one of the test polypeptides in the intein-containing fusion proteins of the present invention. See FIG. 6. This is especially useful when one or both of the test proteins in the intein-containing fusion proteins are believed to contain consensus sequences for certain modifying enzymes. A two-hybrid system involving modifying enzymes has been disclosed in, e.g., U.S. Pat. No. 5,637,463, which is incorporated herein by reference. This system can be applied to the present invention upon appropriate modifications as will be apparent to a skilled artisan apprised of the present disclosure. Examples of useful modifying enzymes include protein kinases which catalyze protein phosphorylation (e.g., serine/threonine phosphorylation, tyrosine phosphorylation by tyrosine kinase, see Lioubin et al., *Genes Dev.,* 10:1084–1095 (1996)); Keegan et al., *Oncogene,* 12:1537–1544 (1996)), fatty acid acylation, ADP-ribosylation, myristylation, and glycosylation. The modifying enzymes can be co-expressed in the host cells with the intein-containing fusion proteins. It is recognized that over-expression of certain modifying enzymes such as tyrosine kinases may be toxic to host cells. This can be avoided by using inducible promoters or weak promoters to drive expression of the toxic modifying enzymes in host cells.

In yet another aspect of the present invention, a kit is provided comprising various vectors and reagents described above. The kit will provide users some convenience in practicing the various embodiments of the present invention. In particular, the kit can be used in detecting and/or characterizing protein-protein interactions. Accordingly, components that can be included in the kit will be apparent to a skilled artisan apprised of the present disclosure. Specifically, any vectors, reagents, and the like described above in connection with various embodiments of the present invention can be included in the kit. Typically, the various components of the kit are placed in a rack, compartmentalized support or enclosed container for purposes of organizing and/or transporting the kit.

In a specific embodiment, the kit includes at least a pair of expression vectors. One expression vector contains a chimeric gene operably linked to a transcription regulatory sequence. The chimeric gene includes a DNA sequence encoding an N-intein and a multiple cloning site (MCS). The multiple cloning site is operably linked to the N-intein coding sequence such that a DNA sequence encoding a test polypeptide of interest can be conveniently inserted in frame into the MCS and a fusion protein can be produced containing the N-intein and the test polypeptide. Likewise, the other expression vector also contains a transcription regulatory sequence operably linked to a chimeric gene which includes a DNA sequence encoding a C-intein and a multiple cloning site (MCS). The multiple cloning site is operably linked to the C-intein coding sequence such that a DNA sequence encoding another test polypeptide of interest can be conveniently inserted in frame into the MCS and a fusion protein can be produced containing the C-intein and the test polypeptide. One or both of the chimeric genes further contain an operably linked DNA sequence encoding an inactive reporter protein capable of being converted to an active reporter protein upon trans-splicing mediated by the N-intein and the C-intein. Various arrangements of the chimeric genes can be used, as will be apparent from the discussions below in connection with the method for detecting protein-protein interactions of the present invention. In a preferred embodiment, specially selected and/or modified coding sequences for the N-intein and C-intein are used such that the N-intein and C-intein do not significantly interact with one another.

The expression vectors may also include other components as described above in connection with the bait vectors and prey vectors of the present invention. For example, the expression vectors may contain elements necessary for the replication of the vector in a host cell, the correct transcription and translation of the chimeric gene (e.g., promoters and other transcriptional regulatory elements, transcription termination signal, etc.). The vectors preferably also contain a selection marker gene for selecting and maintaining only those host cells harboring the vectors.

For application in an intein-based multi-hybrid system of the present invention, the kit may further include one or more additional expression vectors each containing a gene encoding a test protein, e.g., a modifying enzyme (e.g., protein kinase, enzymes catalyzing glycosylation, ribosylation, myristalization, etc.). The gene may be placed under control of a constitutive or inducible promoter.

When the reporter protein is a transcription activator or suppressor, the kit may further comprise a reporting vector. As described above, the reporting vector contains a detectable gene under the control of a promoter specifically activated or repressed by the activator or suppressor, respectively.

In addition, the kit of the present invention can also comprise one or more types of host cells, for example, yeast host strains for the expression of the chimeric genes and other genes. Preferably, yeast strains of opposite yeast mating types (a and α) are provided. The yeast strains should have genotypes suitable for the selection of the various vectors based on the selection marker genes in the vectors, and suitable for the detection of the active reporter generated in the host strains as a result of intein-mediated protein trans-splicing. Optionally, E. coli strains for the amplification of the various vectors are also provided in the kit.

Additionally, the kit may include instructions for using the kit to practice the present invention. The instructions should be in writing in a tangible form or stored as an electronically retrievable form.

As will be apparent to a skilled artisan, any arrangements of the components in the fusion proteins of the present invention can be adopted so long as the protein trans-splicing mediated by the N- and C-intein and initiated by a specific interaction between the test polypeptides can be detected by measuring the active reporter produced during the protein splicing process.

Figure 3A:
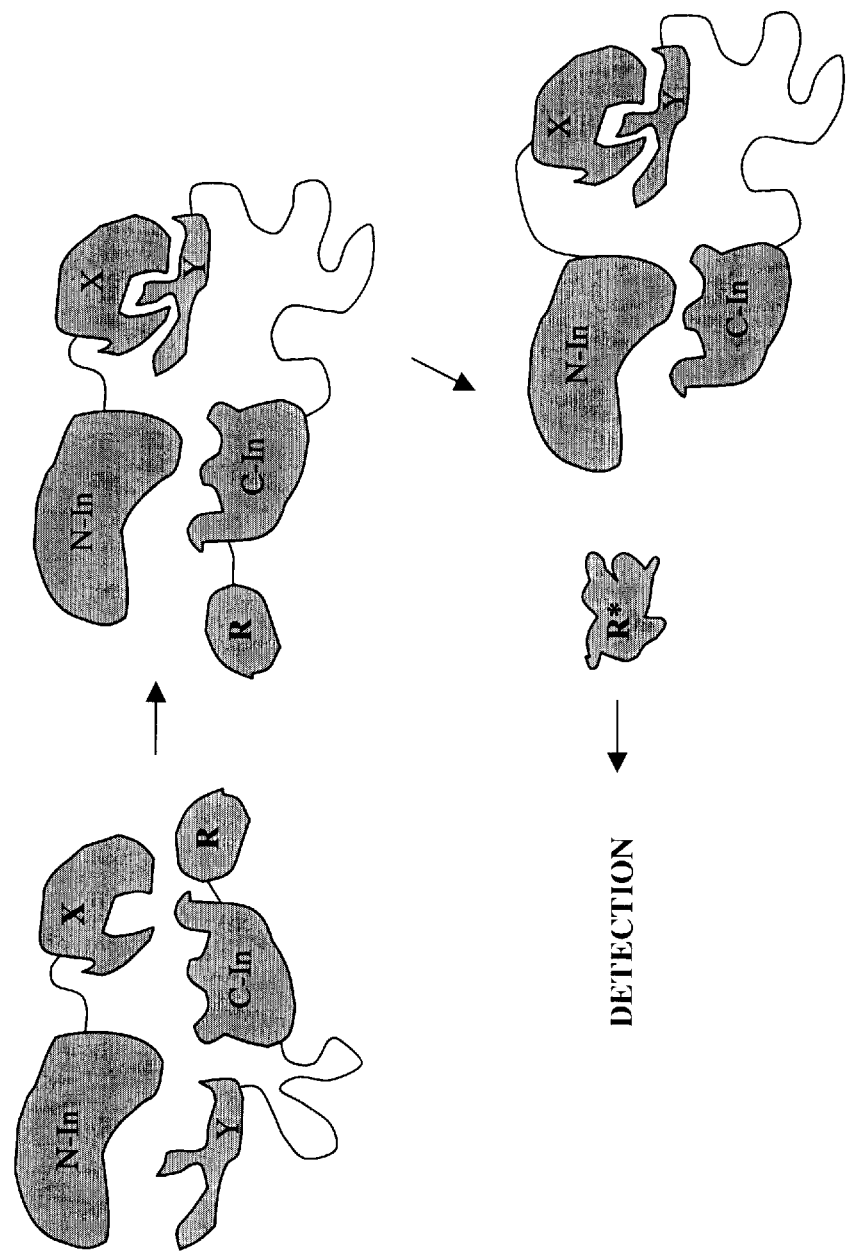
FIGS. 3A–3F are diagrams illustrating the fusion proteins in different embodiments of the present invention.

In one embodiment, as shown in FIG. 3A, one fusion protein has a first test polypeptide X fused or conjugated to the C-terminus of an N-intein, while the other fusion protein has a second test polypeptide Y fused to the N-terminus of a C-intein and a reporter R (inactive) fused to the C-terminus of the C-intein. Upon tans-splicing, the reporter is excised off and becomes a free detectable active reporter R*.

Figure 3B:
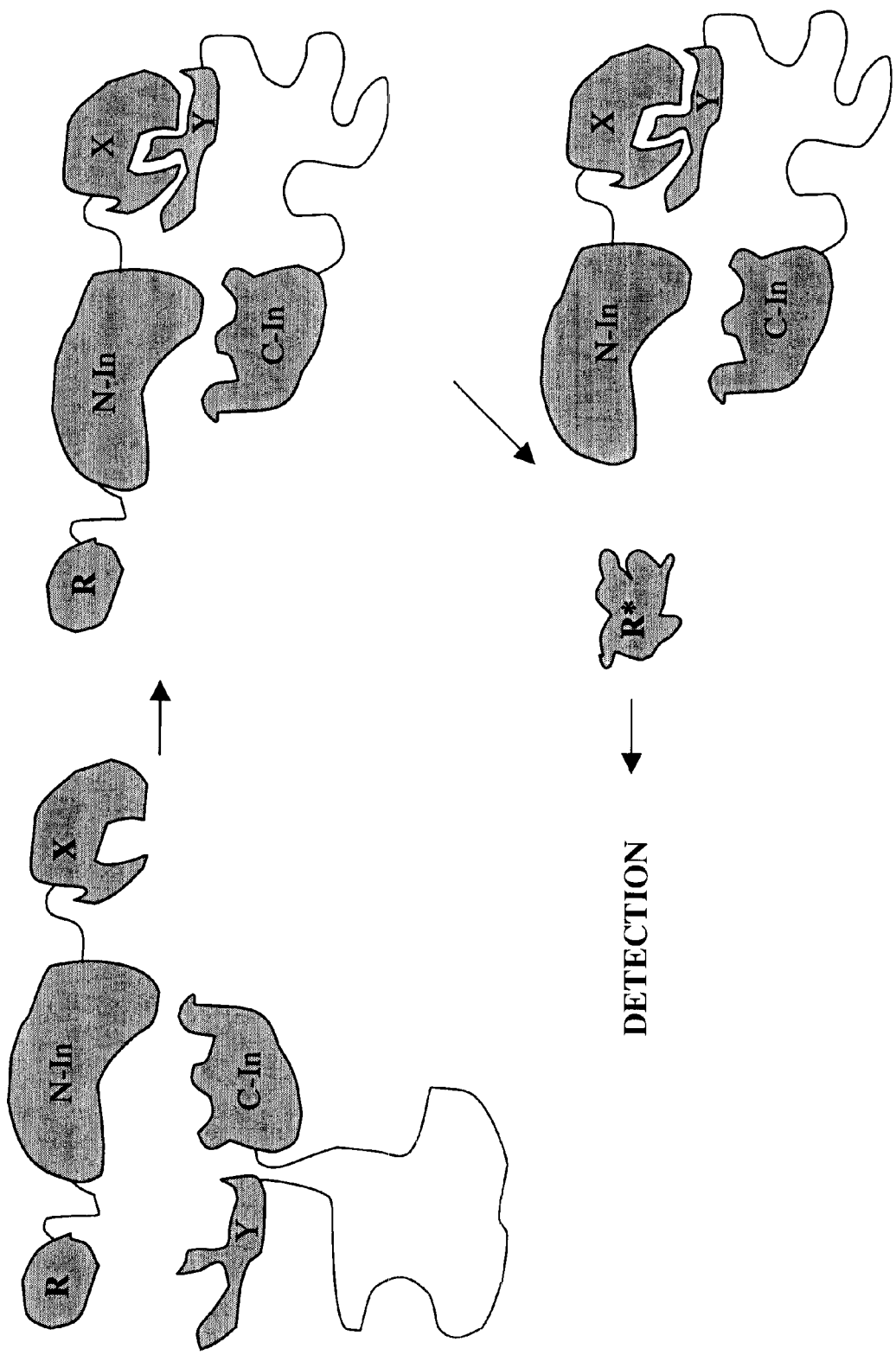

In another embodiment, as shown in FIG. 3B, one fusion protein has a first test polypeptide X fused to the C-terminus of an N-intein and a reporter R (inactive) fused to the N-terminus of the N-intein. The other fusion protein includes a second test polypeptide Y fused to the N-terminus of a C-intein. After trans-splicing mediated by the N- and C-intein, a detectable free active reporter R* is released.

Figure 3C:
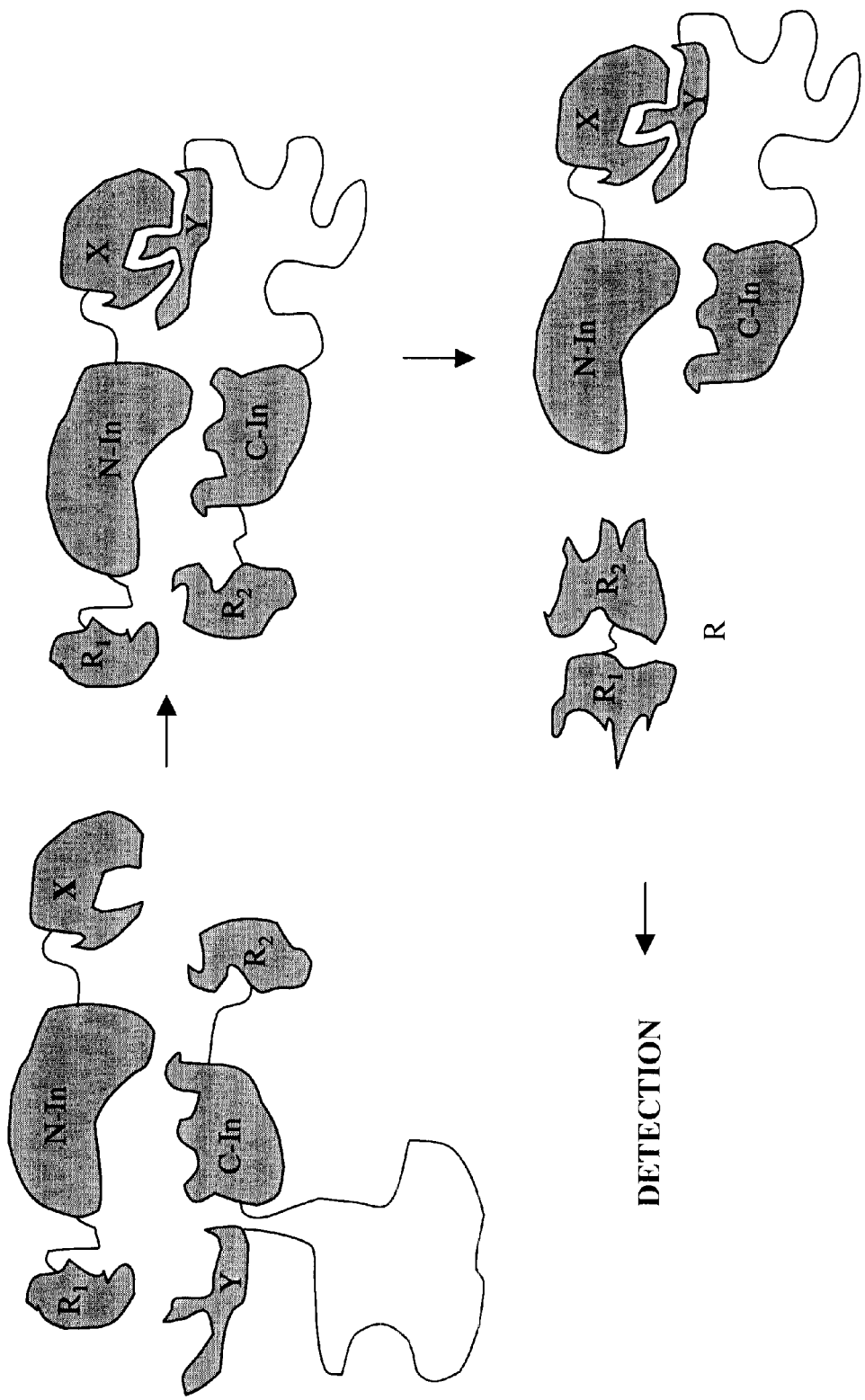

FIG. 3C illustrates the fusion protein arrangement in another embodiment of the invention. The first fusion protein consists of a first portion of a reporter R ($R_1$) fused to the N-terminus of an N-intein and a first test polypeptide (X) fused to the C-terminus of the N-intein. The second fusion protein consists of a second test polypeptide (Y) fused to the N-terminus of a C-intein and the remaining portion of the reporter R ($R_2$) fused to the C-terminus of the C-intein. In this manner, upon intein-directed trans-splicing, the two portions of the reporter R are ligated together thus forming a detectable active reporter R.

Figure 3D:
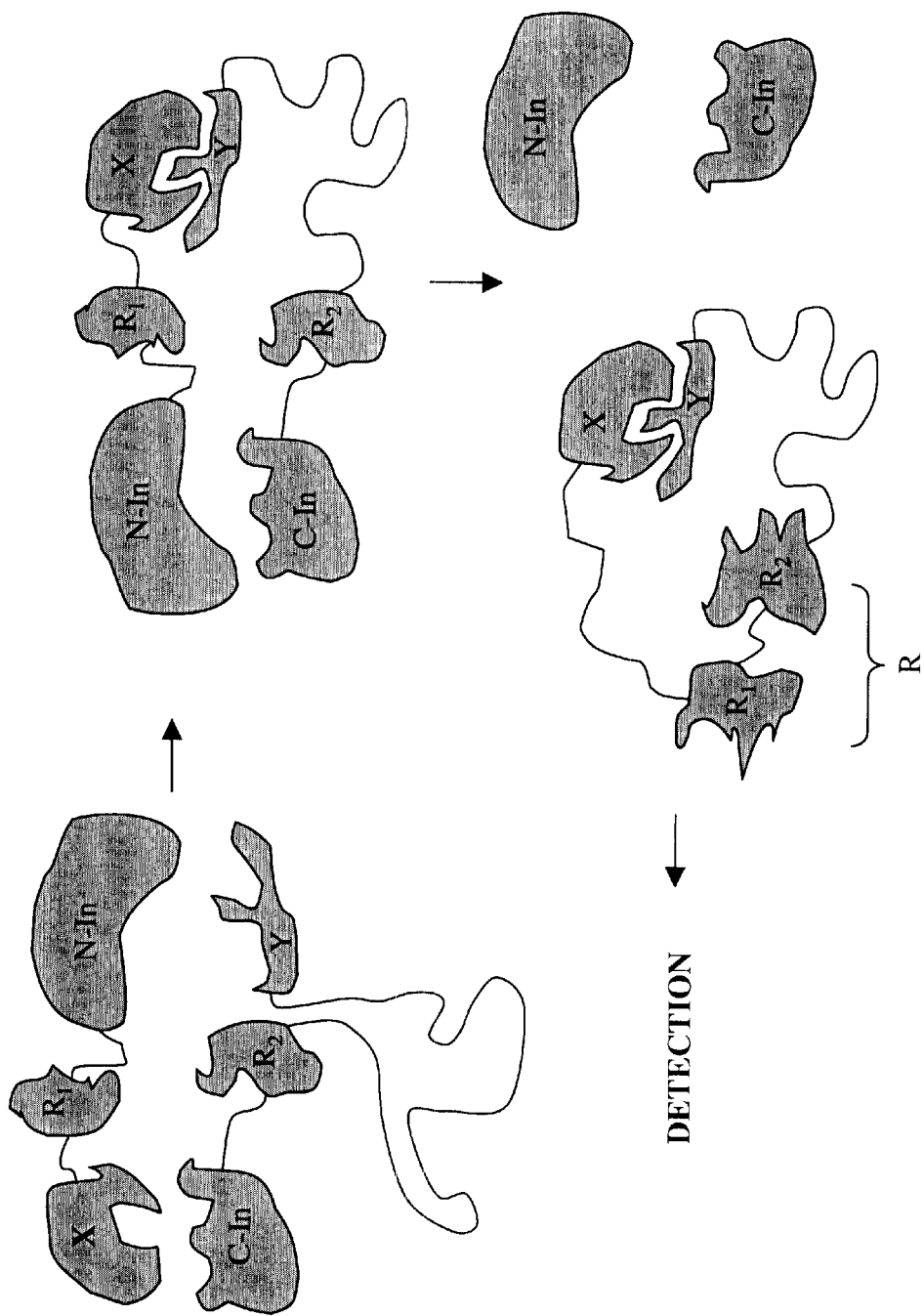

FIG. 3D is a diagram showing the fusion proteins design in yet another embodiment of the present invention. The first fusion protein consists of a first test polypeptide (X) fused to a first portion of a reporter R ($R_1$) which in turn is fused to the N-terminus of an N-intein. The second fusion protein consists of a C-intein, the remaining portion of the reporter R ($R_2$) fused to the C-terminus of a C-intein, and a second test polypeptide (Y) fused to $R_2$. If the test polypeptides X and Y interact with each other to bring the N-intein and C-intein close together, trans-splicing will result in a detectable construct X-R-Y.

Figure 3E:
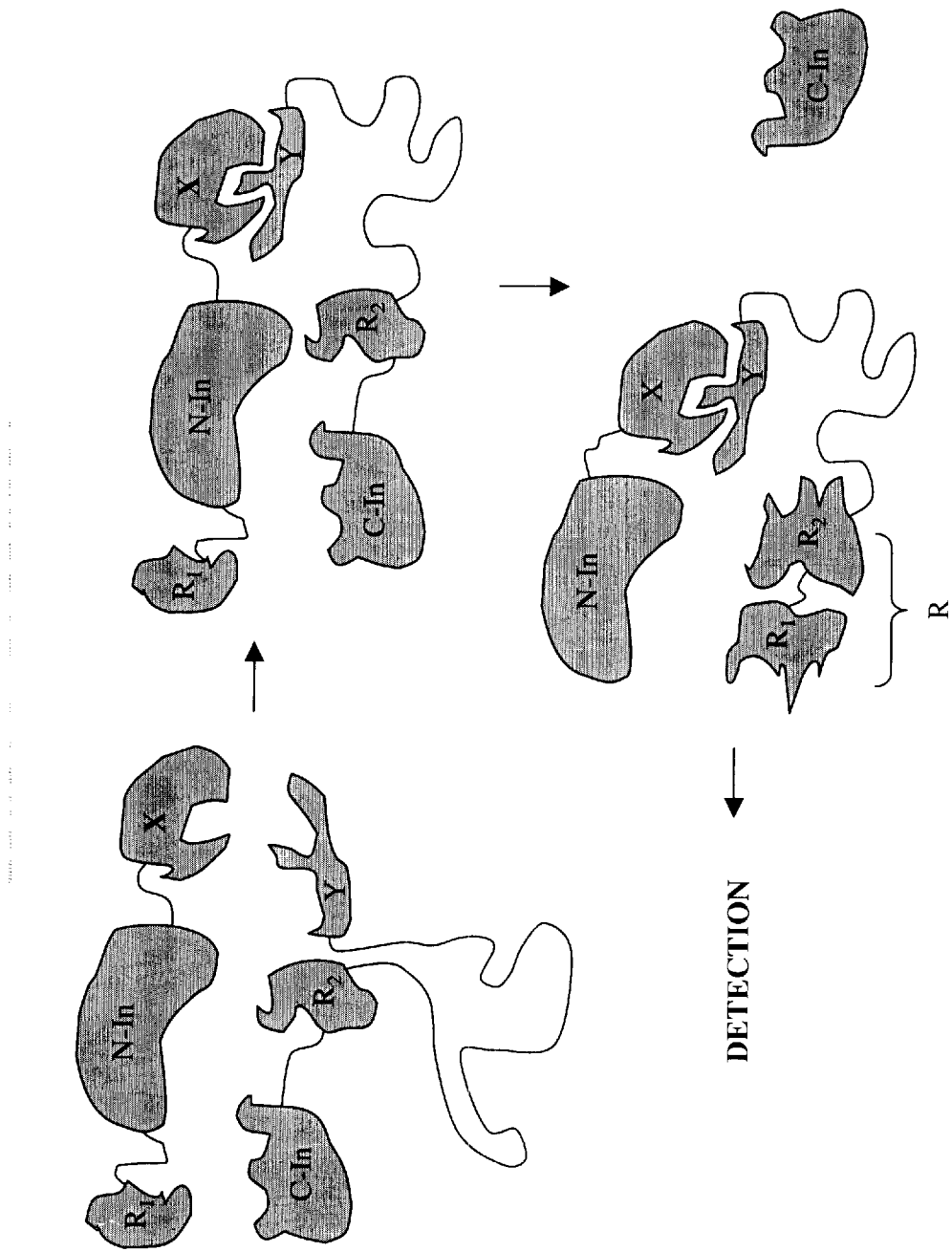

Yet another arrangement of the fusion proteins is demonstrated in FIG. 3E. The first construct is composed of a first portion of a reporter R ($R_1$) fused to the N-terminus of an N-intein and a test polypeptide (X) fused to the C-terminus of the N-intein. The second construct has a C-intein, the remaining portion the reporter R ($R_2$) fused to the C-terminus of the C-intein, and another test polypeptide (Y) fused to $R_2$. Assuming test polypeptides X and Y interact with each other, thus bringing the N-intein and C-intein close together, trans-splicing can occur resulting in a detectable construct R-Y.

Figure 3F:
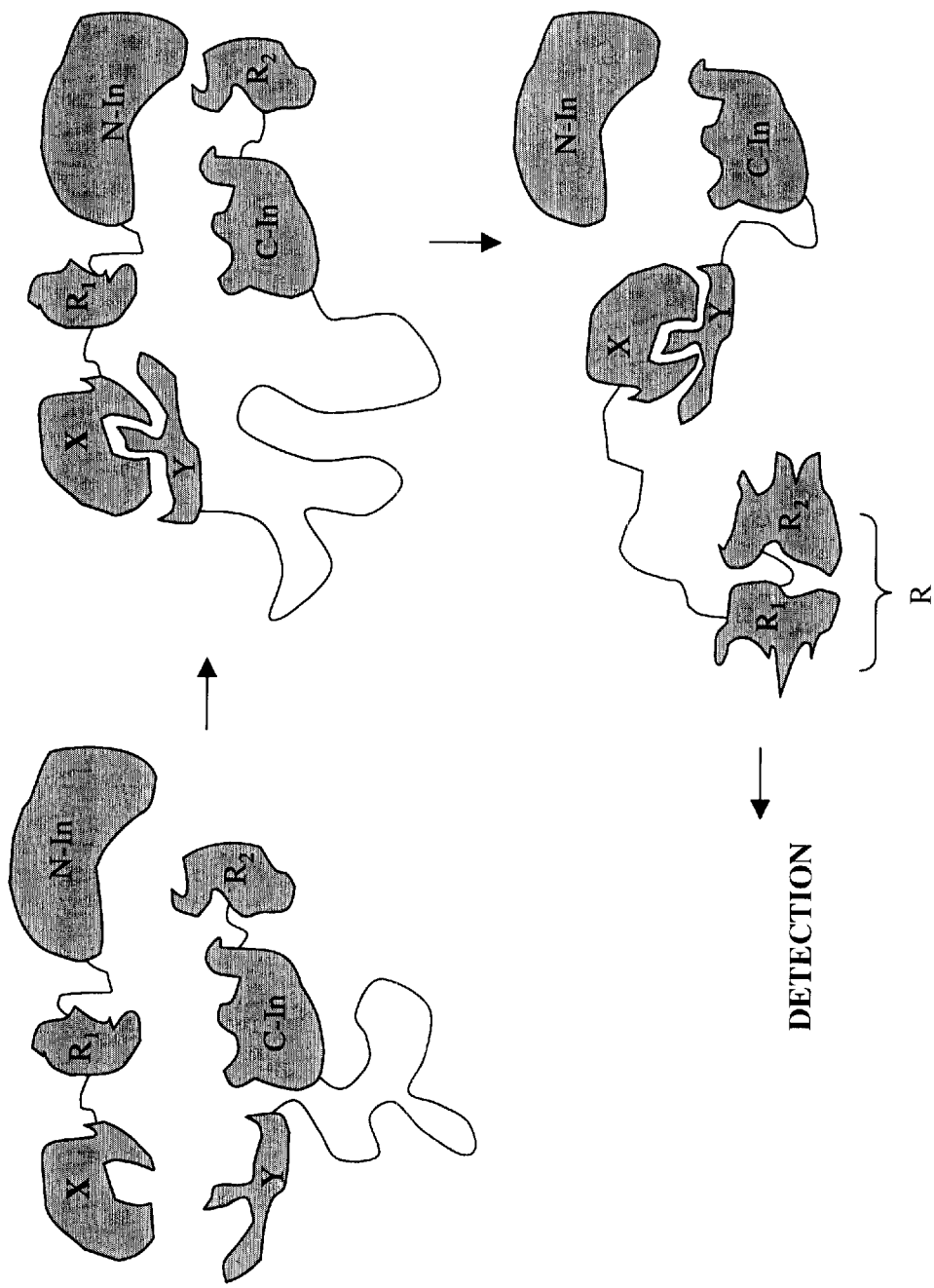

FIG. 3F illustrates yet another possible arrangement of the fusion proteins in the present invention. As shown in FIG. 3F, the first fusion protein has a test polypeptide (X) fused to a first portion of a reporter R ($R_1$) which is in turn fused to the N-terminus of an N-intein. The second fusion protein includes another test polypeptide (Y) fused to the N-terminus of a C-intein and the remaining portion of the reporter R ($R_2$) fused to the C-terminus of the C-intein. Assuming test polypeptides X and Y interact with each other, thus bringing the N-intein and C-intein close together, trans-splicing can occur resulting in a detectable construct X-R.

As is apparent from the above description, the present invention provides a powerful, versatile, intein-based yeast two-hybrid system for detecting and characterizing protein-protein interactions. The system can be used easily adapted to high-throughput screening procedures. In particular, sensitive genetic selection assays can be conveniently incorporated into the system using yeast cells. Detection of protein-protein interaction is based on intein-mediated protein trans-splicing, which is independent of other cellular factors. As a result, the system is useful in detecting biologically relevant protein-protein interactions that occur in any intracellular compartment or even extracellularly. For example, interactions between two nuclear proteins, between between a cytosolic and a membrane-bound protein, between two mitochondrial proteins, between an extracellular and a membrane-bound protein, or between two extracellular proteins can be detected. In addition, protein trans-splicing typically results in changes in protein structures and functions and formation of free new proteins. As a result, various methods available in the art for detecting changes in protein structures and functions can be incorporated into the system allowing great flexibility in fine tuning and optimizing the system, and adapting the system to various applications.

The present invention will be further described by way of the following examples, which are not intended to limit the invention in any manner. Standard techniques well known in the art or the techniques specifically described below were utilized.

EXAMPLE

Figure 8:
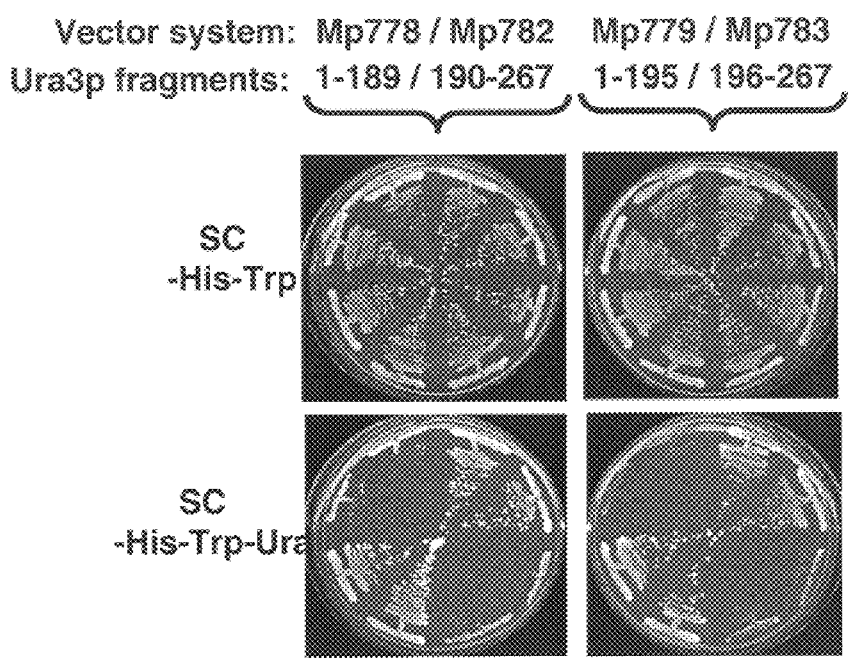
FIG. 8 shows some successful testing results of the intein-based two-hybrid systems demonstrated in the Example.

To test an intein-based two hybrid strategy, we constructed 4 vectors that allow expression of different fusion proteins (see FIG. 8):

1. Mp779. Heterologous sequences can be cloned into a polylinker that permits expression of heterologous protein fragments as a C-terminal fusion to Ura3p and intein fragments. Specifically, the fusion protein encoded by an Mp779-based expression plasmid (designated Mp779-X) will consist of the following fragments, listed from the amino to the carboxy terminus:
   residues 1 to 195 of Ura3p;
   residues 283 to 557 of the VMA1 primary translation product;
   heterologous residues (designated X) of one of two interacting proteins.

2. Mp783. Heterologous sequences can be cloned into a polylinker that permits expression of heterologous protein fragments as an N-terminal fusion to intein and Ura3p fragments. Specifically, the fusion protein encoded by an Mp783-based expression plasmid (designated Mp783-Y) will consist of the following fragments, listed from the amino to the carboxy terminus:
   heterologous protein fragment (designated Y) that interacts with X;
   residues 559 to 738 of the VMA1 primary translation product;
   residues 196 to 267 (the genuine C-terminus) of Ura3p 3. Mp778. Heterologous sequences can be cloned into a polylinker that permits expression of heterologous protein fragments as a C-terminal fusion to Ura3p and intein fragments. Specifically, the fusion protein encoded by an Mp778-based expression plasmid (designated Mp778-X) will consist of the following fragments, listed from the amino to the carboxy terminus:
   residues 1 to 189 of Ura3p;
   residues 283 to 557 of the VMA1 primary translation product;
   heterologous residues (designated X).

4. Mp782. Heterologous sequences can be cloned into a polylinker that permits expression of heterologous protein fragments as an N-terminal fusion to intein and Ura3p fragments. Specifically, the fusion protein encoded by an Mp782-based expression plasmid (designated Mp782-Y) will consist of the following fragments, listed from the amino to the carboxy terminus:
   heterologous protein fragment (designated Y) that interacts with X;
   residues 559 to 738 of the VMA1 primary translation product;
   residues 196 to 267 (the genuine C-terminus) of Ura3p Using these vectors and the human genes encoding the interacting proteins BclX and Bad, we constructed the following expression plasmids:
1. Mp778-BclX
2. Mp778-Bad
3. Mp782-BclX
4. Mp782-Bad
5. Mp779-BclX
6. Mp779-Bad
7. Mp783-BclX
8. Mp783-Bad.

Figure 9:
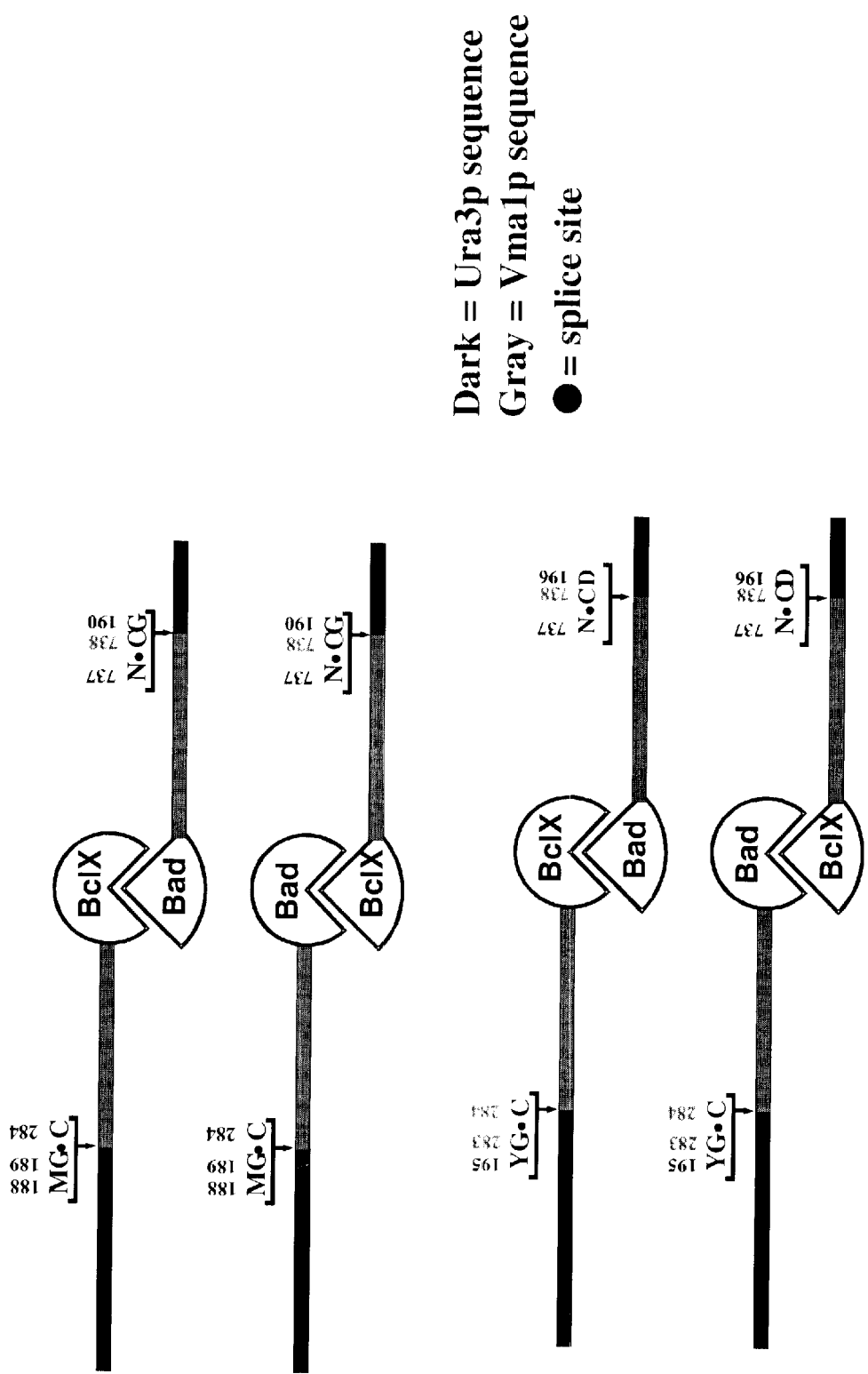
FIG. 9 illustrates the protein-protein interactions that give rise to functional Ura3p in the intein-based two-hybrid systems demonstrated in the Example.

Yeast (genotype: his3Δ200 leu2Δ0 met15Δ0 trp1Δ63 ura3Δ0) were transformed with combinations of these expression plasmids and their parental vectors to test for reconstitution of Ura3p activity that was dependent on BclX-Bad association. Two independent clones from each transformation were streaked onto media selective for Ura3p activity (SC-His-Trp-Ura) or selective only for the presence of the plasmids (SC-His-Trp). As shown in FIG. 9, yeast transformed with pairs of plasmids encoding fusion proteins that could, presumably via protein splicing, reconstitute full length Ura3p exhibited uracil prototrophy. Specifically, yeast co-transformed with the following plasmids could grow on uracil-deficient media:
   Mp778-BclX and Mp782-Bad
   Mp778-Bad and Mp782-BclX
   Mp779-BclX and Mp783-Bad
   Mp779-Bad and Mp783-BclX A cartoon of the protein-protein interactions that are presumed to give rise to functional Ura3p is shown in FIG. 10. Notably, the uracil prototrophy was independent of "orientation" of the two-hybrid interaction; that is, it was seen whether BclX was fused to the N-terminal intein fragment and Bad was fused to the C-terminal intein fragment or vice versa. No growth was observed when strains lacked either the BclX- or Bad-containing fusion.

All publications and patent applications mentioned in the specification are indicative of the level of those skilled in the art to which this invention pertains. All publications and patent applications are herein incorporated by reference to the same extent as if each individual publication or patent application was specifically and individually indicated to be incorporated by reference.

Although the foregoing invention has been described in some detail by way of illustration and example for purposes of clarity of understanding, it will be obvious that certain changes and modifications may be practiced within the scope of the appended claims.

What is claimed is:

1. A method for detecting protein-protein interaction between a first test polypeptide and a second test polypeptide, comprising:
   producing in a yeast cell a first fusion protein and a second fusion protein, said first fusion protein having said first test polypeptide and an N-intein, said second fusion protein having said second test polypeptide and a C-intein, wherein at least one of the two fusion proteins has an inactive reporter capable of being converted to an active reporter protein upon trans-splicing through said N-intein and said C-intein; and
   determining the production of said active reporter protein.

2. A method for detecting protein-protein interaction between a first test polypeptide and a second test polypeptide, comprising:
   introducing into an yeast cell a first chimeric gene and a second chimeric gene, said first chimeric gene encoding a first fusion protein having said first test polypeptide, an N-intein, and a first inactive reporter polypeptide fused to the N-terminus of an N-intein, said second chimeric gene encoding a second fusion protein having said second test polypeptide, a C-intein, and a second inactive reporter polypeptide fused to the C-terminus of said C-intein, wherein ligation between the C-terminus of said first inactive reporter polypeptide and the N-terminus of said second inactive reporter polypeptide forms an active reporter protein;

expressing said first fusion protein and said second fusion protein in said yeast cell; and detecting said active reporter protein.

3. The method of claim 2, wherein said first inactive reporter polypeptide is an N-terminal fragment of said active reporter protein and said second inactive reporter polypeptide is the remaining C-terminal fragment of said active reporter protein.

4. The method of claim 2, wherein said yeast cell is a diploid cell and said step of introducing into said yeast cell said first chimeric gene and said second chimeric gene comprises mating a first haploid yeast cell having said first chimeric gene with a second haploid yeast cell having said second chimeric gene.

5. The method of claim 2, wherein said first test polypeptide is fused to the C-terminus of said N-intein in said first fusion protein, and said second test polypeptide is fused to the N-terminus of said C-intein in said second fusion protein.

6. The method of claim 2, wherein said first test polypeptide is fused to the N-terminus of said first inactive reporter polypeptide in said first fusion protein, and said second test polypeptide is fused to the N-terminus of said C-intein in said second fusion protein.

7. The method of claim 2, wherein said first test polypeptide is fused to the C-terminus of said N-intein in said first fusion protein, and said second test polypeptide is fused to the C-terminus of said second inactive reporter polypeptide in said second fusion protein.

8. The method of claim 2, wherein said first test polypeptide is fused to the N-terminus of said first inactive reporter polypeptide in said first fusion protein, and said second test polypeptide is fused to the C-terminus of said second inactive reporter polypeptide in said second fusion protein.

9. The method of claim 2, wherein said active reporter protein is detectable by a color assay.

10. The method of claim 2, wherein said active reporter protein is an auxotrophic protein and is detectable by a cell viability assay.

11. The method of claim 2, wherein the expression of at least one of said fusion proteins in said yeast cell is inducible and occurs only when said yeast cell is subject to a predetermined condition.

12. The method of claim 2, wherein said active reporter protein is a transcription activator and said yeast cell further comprises a detectable gene that is activated when said transcription activator is present.

13. The method of claim 2, wherein said active reporter protein is a transcription repressor and said yeast cell further comprises a detectable gene that is repressed when said transcription repressor is present.

14. The method of claim 2, further comprising introducing into said yeast cell a nucleic acid encoding a third test polypeptide.

15. The method of claim 2, further comprising introducing into the yeast cell a small organic compound to allow said small organic compound to interact with either said first or second test polypeptide or both.

16. The method of claim 9, wherein said active reporter protein is selected from the group consisting of β-galactosidase, luciferase, green fluorescence protein, blue fluorescence protein, alkaline phosphatase, and horseradish peroxidase.

17. The method of claim 14, wherein the interaction between said first and second test polypeptide requires the presence of said third test polypeptide.

18. The method of claim 14, herein said third test polypeptide modifies post-translationally at least one of said first and second test polypeptides.

19. A method for detecting an interaction between a first test polypeptide and a second test polypeptide, comprising:

conducting a detection assay comprising the steps of (a) producing in a yeast cell a first fusion protein and a second fusion protein, said first fusion protein having said first test polypeptide and an N-intein, said second fusion protein having said second test polypeptide and a C-intein, wherein at least one of the two fusion proteins has an inactive reporter capable of being converted to an active reporter protein upon trans-splicing through said N-intein and said C-intein; and (b) determining the production of said active reporter protein in said yeast cell;

conducting a control assay in which the interaction between the first and second test polypeptides in said fusion proteins in said detection assay is preempted; and comparing the level of said active reporter in said detection assay and said control assay.

20. The method of claim 19, wherein said control assay comprises:

allowing said first test polypeptide in said first fusion protein to interact with said second test polypeptide in said second fusion protein in the presence of an inhibitor of said interaction; and detecting the active reporter.

21. The method of claim 19, wherein said control assay comprises the steps of:

producing in a second yeast cell a third and fourth fusion proteins, wherein said third fusion protein is same as said first fusion protein except that said third fusion protein has a third test polypeptide but not said first test polypeptide, said fourth fusion protein is same as said second fusion protein except that said fourth fusion protein has a fourth test polypeptide but not said second test polypeptide, and wherein said third and fourth test polypeptides do not interact with each other; and detecting said active reporter protein.

22. The method of claim 19, wherein said control assay comprises the steps of:

producing in another yeast cell a third fusion protein and a fourth fusion protein, wherein said third fusion protein is same as said first fusion protein except that said third fusion protein lacks said first test polypeptide, said fourth fusion protein is same as said second fusion protein except that said fourth fusion protein lacks said second test polypeptide; and detecting said active reporter protein.

23. A kit comprising:

a first vector containing a first chimeric gene encoding a first inactive reporter polypeptide fused to the N-terminus of an N-intein and containing an operably linked first multiple cloning site (MCS) such that when a nucleic acid encoding a first test polypeptide is inserted into said first multiple cloning site, said first chimeric gene is capable of expressing a fusion protein containing said N-intein, said first test polypeptide, and said first inactive reporter polypeptide fused to the N-terminus of said N-intein;

a second vector containing a second chimeric gene encoding a second inactive reporter polypeptide fused to the C-terminus of a C-intein and containing an operably linked second multiple cloning site (MCS) such that when a nucleic acid encoding a second test polypeptide is inserted into said second multiple cloning site, said second chimeric gene is capable of expressing a fusion protein containing said C-intein, said second test polypeptide, and said second inactive reporter polypeptide fused to the C-terminus of said C-intein, wherein ligation between the C-terminus of said first inactive reporter polypeptide and the N-terminus of said second inactive reporter polypeptide forms an active reporter protein; and a yeast cell deficient in said active reporter protein.

24. The kit of claim 23, wherein said active reporter protein is a functional orotidine-5'-phosphate decarboxylase, said first inactive reporter polypeptide is an N-terminal portion of orotidine-5'-phosphate decarboxylase, said second inactive reporter polypeptide is a C-terminal portion of orotidine-5'-phosphate decarboxylase, and said yeast cell lacks a functional URA3 gene.

25. The kit of claim 23, wherein said active reporter protein is a transcriptional activator, and said kit further comprises a reporting vector having a detectable gene the expression of which is enhanced by said transcriptional activator.

26. The kit of claim 23, wherein said active reporter protein is a transcriptional repressor, and said kit further comprises a reporting vector having a detectable gene the expression of which is repressed by said transcriptional repressor.

27. A kit comprising:

a first expression vector containing a first chimeric gene having from 5' to 3' operably linked in the same open reading frame: (a) a sequence encoding a first inactive reporter polypeptide; (b) a coding sequence for an N-intein; and (c) a first multiple cloning site; and a second expression vector containing a second chimeric gene having from 5' to 3' operably linked in the same open reading frame: (a) a second multiple cloning site; (b) a coding sequencing for a C-intein; (c) a sequence encoding a second inactive reporter polypeptide, wherein ligation between the C-terminus of said first inactive reporter polypeptide and the N-terminus of said second inactive reporter polypeptide forms an active reporter.

28. A kit comprising:

an expression vector containing a chimeric gene having operably linked in the same open reading frame: (a) a sequence encoding a first inactive reporter polypeptide; (b) a coding sequence for an N-intein or C-intein; and (c) a multiple cloning site; and an expression library expressing a plurality of fusion proteins, each of said fusion proteins having: (a) a polypeptide; (b) a C-intein or N-intein; and (c) a second inactive reporter polypeptide, wherein ligation between said first and second inactive reporter polypeptides forms an active reporter protein.

* * * * *